US011103639B1

(12) United States Patent
Chen et al.

(10) Patent No.: US 11,103,639 B1
(45) Date of Patent: Aug. 31, 2021

(54) TWO-COMPONENT SYRINGE

(71) Applicants: Xiaodi Chen, Webster, NY (US); Xinyi Cai, Atlanta, GA (US)

(72) Inventors: Xiaodi Chen, Webster, NY (US); Xinyi Cai, Atlanta, GA (US)

(73) Assignees: Xiaodi Chen, Webster, NY (US); Xinyi Cai, Stamford, CT (US)

( * ) Notice: Subject to any disclaimer, the term of this patent is extended or adjusted under 35 U.S.C. 154(b) by 0 days.

(21) Appl. No.: 17/151,159

(22) Filed: Jan. 16, 2021

(51) Int. Cl.
*A61M 5/19* (2006.01)
*A61M 5/31* (2006.01)
*A61J 1/20* (2006.01)

(52) U.S. Cl.
CPC .............. *A61M 5/19* (2013.01); *A61J 1/2093* (2013.01); *A61M 5/3129* (2013.01); *A61M 2202/064* (2013.01)

(58) Field of Classification Search
CPC ...... A61M 5/19; A61M 5/178; A61M 5/2066; A61M 5/2448; A61M 5/3129; A61M 2005/2451; A61M 5/284; A61M 5/31596; A61M 5/3294; A61M 3/005; A61M 2005/2073; A61J 1/2089; A61J 1/2093; A61J 1/2096; A61J 1/20
See application file for complete search history.

(56) References Cited

U.S. PATENT DOCUMENTS

| | | | |
|---|---|---|---|
| 2,761,447 A * | 9/1956 | Hersee | A61M 5/2448 604/89 |
| 3,016,896 A | 1/1962 | Van Sickle | |
| 3,477,431 A * | 11/1969 | Walecka | A61M 5/284 604/89 |
| 4,573,976 A * | 3/1986 | Sampson | A61M 5/3269 604/198 |
| 4,599,082 A | 7/1986 | Grimard | |

* cited by examiner

*Primary Examiner* — Brandy S Lee
*Assistant Examiner* — Hong-Van N Trinh
(74) *Attorney, Agent, or Firm* — Tracy Jong Law Firm; Tracy P. Jong; Cheng Ning Jong

(57) ABSTRACT

A syringe including a first hollow cylinder including a first end, a second end and a first inner diameter; a second hollow cylinder including a first end, a second end and a second inner diameter, wherein the second end of the second hollow cylinder is fixed with respect to the first end of the second hollow cylinder; a tube including a first end having the first inner diameter and a second end having the second inner diameter, wherein the tube is configured to connect the first hollow cylinder at the second end of the first hollow cylinder and the second hollow cylinder at the first end of the second hollow cylinder; and a piston configured to slide within the first hollow cylinder, the tube and the second hollow cylinder.

6 Claims, 19 Drawing Sheets

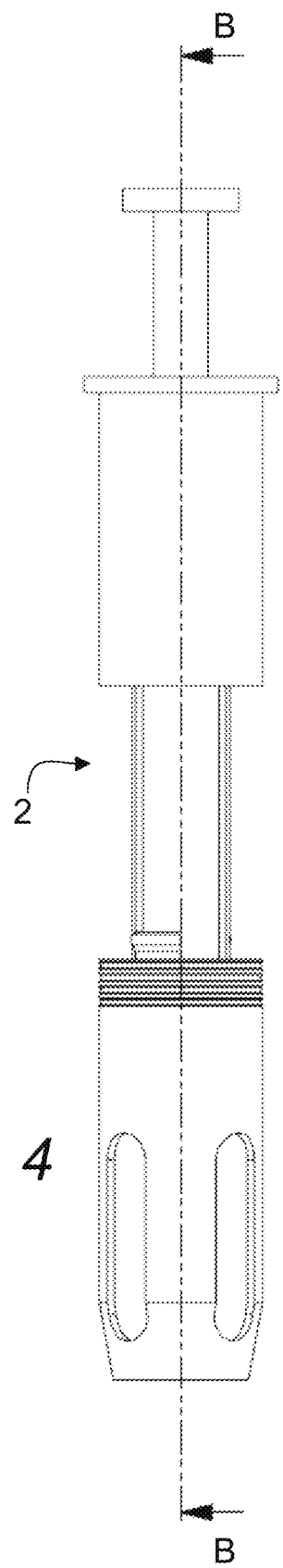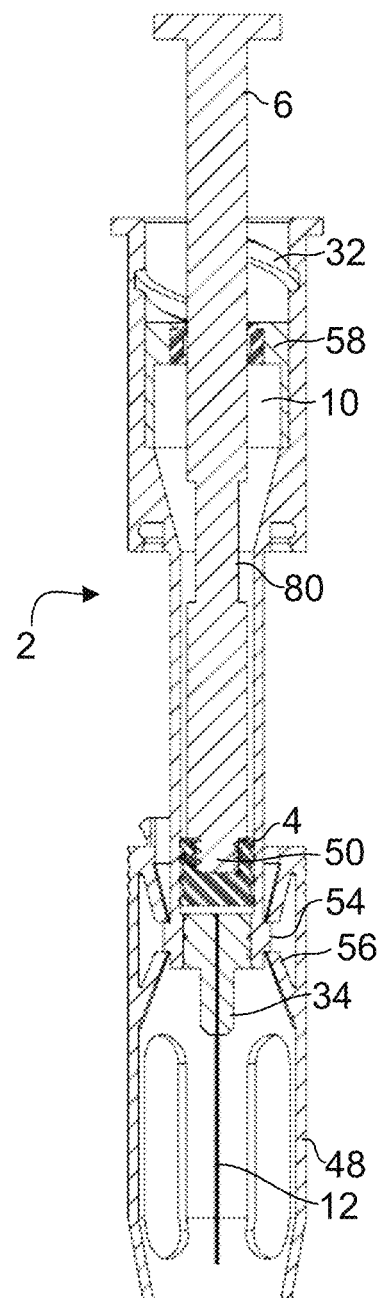
FIG. 4
FIG. 5

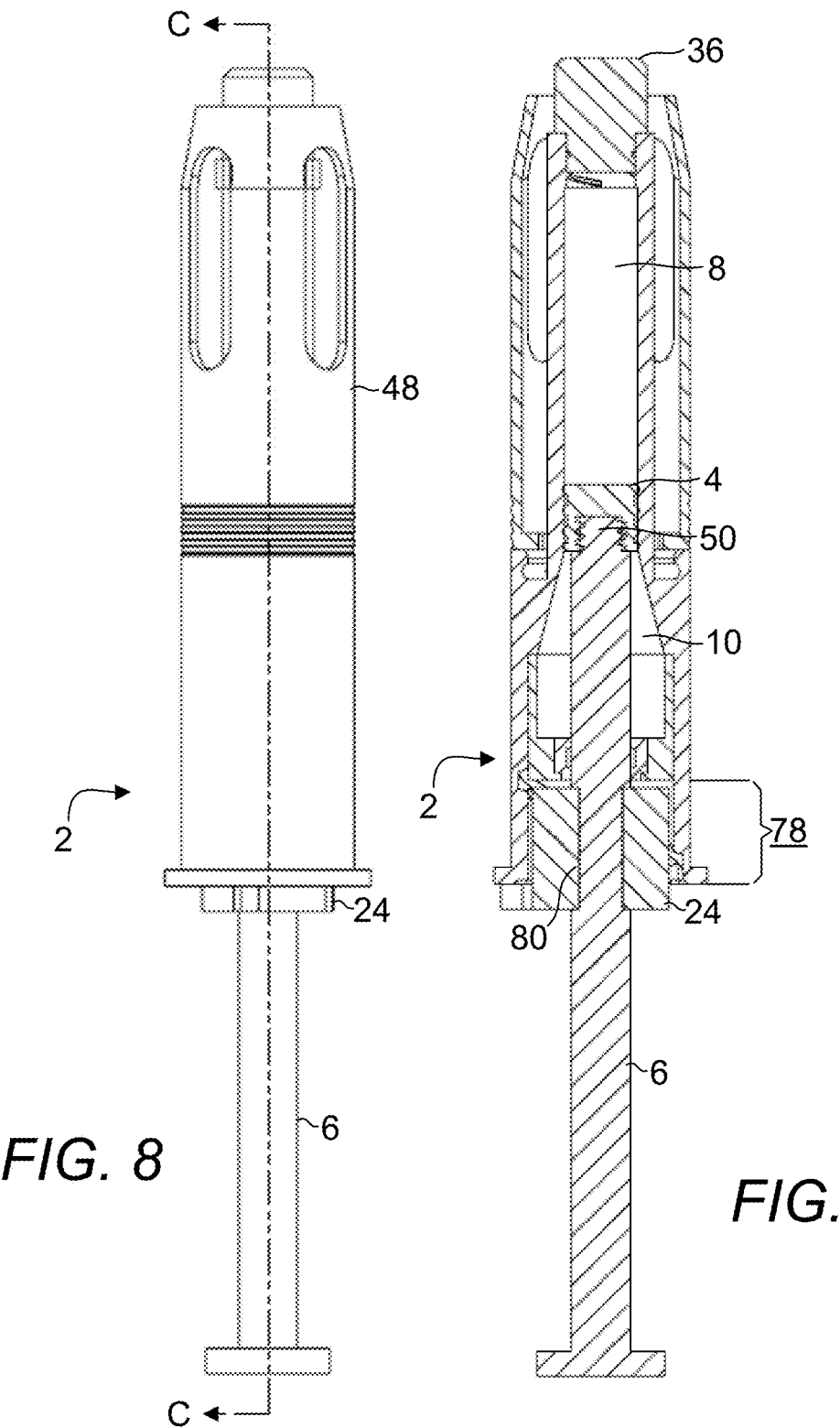

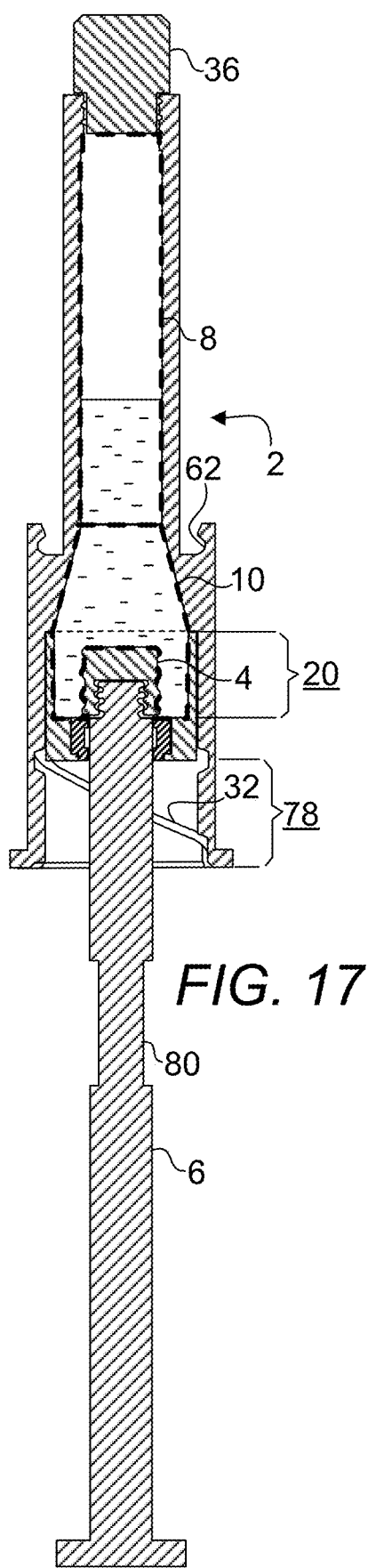
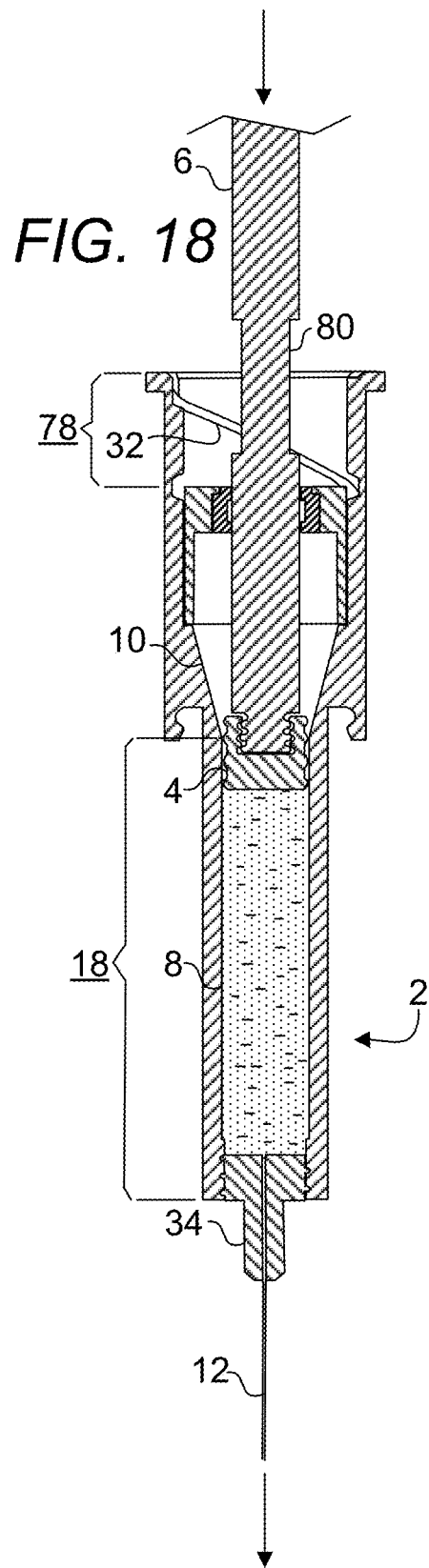
FIG. 17
FIG. 18

TWO-COMPONENT SYRINGE

BACKGROUND OF THE INVENTION

1. The Field of the Invention

The present invention relates to a syringe useful for reconstituting a component to form a mixture to be applied with a needle. More specifically, the present invention is directed to a syringe useful for effectively mixing two components held therein or held in two different ambient conditions to form a mixture to be applied with a needle.

2. Background Art

Vaccines and medications that require reconstitution, e.g., COVID-19 vaccines, are often kept separately in two different vials. The primary benefit of separating the components is to increase shelf life; these products are often unstable after a short period of time after reconstitution. The traditional packaging method can be taxing on healthcare workers and provide multiple disadvantages. The process is time-consuming, increases waste, and error prone.

Before administering these products, trained and authorized personnel must follow the reconstitution procedure. Both vial stoppers must be cleaned with alcohol pads. A sterile needle and syringe are then used to withdraw the liquid component, e.g., from a first vial. The contents of the syringe are then transferred into the dry component, e.g., in a second vial. The second vial is then gently shaken thoroughly until the contents are dissolved. The vial contents are then withdrawn and inspected for impurities before it is ready to be used. This procedure is a time-consuming process and can slow down workflow in a hospital, clinic and pharmacy, etc.

Wastes generated from a conventional reconstitution includes two vials, two vial caps, one needle, time wasted during product preparation, and any reconstituted products that have lost their efficacies. The raw materials required to house the two different components alone are a noticeable waste compared to having one pre-filled syringe. The opportunity cost of conventional reconstitutions varies depending on which healthcare professionals are preparing the products; nevertheless, the time and attention needed to prepare the reconstituted products can be invested in other parts of the workflow to prepare an injectable material.

According to International Safety Center Exposure Prevention Information Network (EPINet®) Report for Needlestick, when looking at devices associated with percutaneous injuries, 24.5% of all reported injuries are from disposable syringes, while only 1.20% are from pre-filled syringes.

U.S. Pat. No. 3,016,896 to Van Sickle (hereinafter Van Sickle) discloses a hypodermic syringe for use in treating human beings as well as animals. Van Sickle discloses a syringe with a mixing chamber that does not encompass a first volume in which a liquid is held and a second volume in which a powder material is held. As the skirt (74 of Van Sickle) is fixedly attached to the plunger (52 of Van Sickle), the skirt (74 of Van Sickle) cannot be pulled sufficiently far to clear the area where the inner diameter of the main body portion (58 of Van Sickle) transitions from a first dimension to a second dimension. It shall also be noted that in Van Sickle, the powder material is disposed at the needle end of a Van Sickle's syringe. As such, a poorly mixed powder material or clumping of the powder material, due potentially to moisture intrusion, can potentially cause plugging of the needle hole, preventing the mixture from exiting the syringe efficiently.

WIPO Pub. No. 2007034020 of Rolla (hereinafter Rolla) discloses a unit for mixing and supplying injectable substances including a plurality of chambers with different cross-sections which are disposed consecutively from smallest to biggest in an axial direction from the injection end. Injectable substances that are mixed when the chambers are communicated following the reverse movement of separating means and a piston which are moved by a coaxial rod that is disposed in the unit. Again, it shall also be noted that in Rolla, the powder material is disposed at the needle end of a Rolla's syringe. As such, a poorly mixed powder material or clumping of the powder material, due potentially to moisture intrusion, can potentially cause plugging of the needle hole, preventing the mixture from exiting the syringe efficiently. Further, as the rod diameter is significantly smaller than the piston diameter, undissolved powder can potentially be disposed on the rod side of the plunger, preventing the plunger from being retracted fully to allow proper mixing of the powder and liquid.

U.S. Pat. No. 3,477,431 to Walecka (hereinafter Walecka) discloses a combined syringe and plural-compartment container for storing solid and liquid ingredients separately for subsequent mixing and injection. The syringe barrel includes an enlarged portion around its periphery at about the center of its longitudinal dimension, and together with the syringe pistons forms a plural-compartment container. When two pistons are used, one of the pistons is positioned immediately adjacent to the enlarged portion of the syringe barrel and the other seals off the open end of the barrel, thus forming two compartments, each of which may contain a different ingredient. By depressing the syringe plunger slightly so that the one piston extends into the enlarged portion of the barrel, a flow path is provided whereby the two ingredients can mix. Lock means are also provided in Walecka in order to prevent accidental displacement of the plunger during transport and storage. FIG. 6 of Walecka discloses a two-compartment syringe where communication between the two components in the two compartments are separated by a piston. It shall be noted however that one of the drawbacks of Walecka's device is the rod end bore diameter which allows a mixture to be inadvertently trapped. It shall be noted that the main body portion 70 is fixedly attached to the rod or is part of the rod. As such, the total volume allowed for mixing is limited to the space between a retracted position of the piston and the dispensation tip of the syringe.

Chinese Pat. App. Pub. No. CN211561395U of Xing et al. (hereinafter Xing) discloses an injector with powder-liquid hybrid chamber. Xing discloses the concept of retracting the rod of a syringe to establish communication between two substances disposed in two different compartments although Xing's device could not have worked well for mixing a liquid and a solid material.

U.S. Pat. No. 4,599,082 to Grimard (Hereinafter Grimard) discloses a two-component syringe includes a barrel having a chamber for retaining fluid and a distal end of the barrel having a passageway therethrough communicating with the chamber. A by-pass stopper is slidably positioned in fluid-tight engagement inside the barrel. The stopper has a distal rib contacting the barrel, a recess on the proximal side of the rib and a groove in the rib for allowing fluid communication between the recess and the chamber. This groove is positioned angularly with respect to the longitudinal access of the barrel so that liquid passing therethrough is directed angularly with respect to the longitudinal axis of the barrel. The barrel also includes a raised peripheral portion serving as a by-pass and defining a by-pass zone. The by-pass zone is shorter than the length of the stopper along the longitudinal axis of the barrel. The by-pass is sufficiently long and raised enough to allow liquid to flow around the stopper between the proximal end of the stopper and the recess when the proximal end of the stopper is positioned in the by-pass zone. Also included is a piston slidably positioned in fluid-tight engagement inside the barrel. This piston is adapted to engage a plunger rod to facilitate its operation. Grimard's device functions according to a principle similar to Walecka's device although the rod is "extended" to activate mixing in Grimard's device while the rod is "retracted" to activate mixing in Walecka's device.

There exists a need for a syringe capable of holding more than one component therewithin where the components may be mixed efficiently to form a mixture or a component may be reconstituted just prior to its use with actions that are already familiar to the user.

SUMMARY OF THE INVENTION

In accordance with the present invention, there is provided a syringe including:
(a) a first hollow cylinder including a first end, a second end and a first inner diameter;
(b) a second hollow cylinder including a first end, a second end and a second inner diameter, wherein the second end of the second hollow cylinder is fixed with respect to the first end of the second hollow cylinder;
(c) a tube including a first end having the first inner diameter and a second end having the second inner diameter, wherein the tube is configured to connect the first hollow cylinder at the second end of the first hollow cylinder and the second hollow cylinder at the first end of the second hollow cylinder; and
(d) a piston configured to slide within the first hollow cylinder, the tube and the second hollow cylinder, a first position of the piston within the first hollow cylinder defining a first space between the piston and the first end of the first hollow cylinder and a second space between the piston and the second end of the second hollow cylinder, wherein the first space is isolated from the second space, wherein a communication of a first substance within the first space and a second substance within the second space is enabled through the tube by withdrawing the piston from the first space and the communication is configured to occur in a total volume of at least a combined volume of the first space and the second space.

In one embodiment, the syringe further includes a needle disposed on the first end of the first hollow cylinder for delivering at least one of the first substance and a mixture of the first substance and the second substance. In one embodiment, the syringe further includes a rod attached to the piston and a skirt extending from the second end of the second hollow cylinder and a stopper removably attached to the rod and the skirt to prevent accidental movement between the rod and the first hollow cylinder. In one embodiment, the syringe further includes a rod attached to the piston and a skirt extending from the second end of the second hollow cylinder and a stopper removably attached to the rod and the skirt to allow a first action to remove the stopper to correspond to a second action that enables the communication. In one embodiment, the syringe further includes a rod attached to the piston and a stopper removably attached to the rod and the second hollow cylinder to prevent accidental movement between the rod and the first hollow cylinder. In one embodiment, the syringe further includes a rod attached to the piston and a stopper removably attached to the rod and the second hollow cylinder to allow a first action to remove the stopper to correspond to a second action that enables the communication. In one embodiment, the second end of the first hollow cylinder is configured to be removably attached to the first end of the tube with an attachment mechanism. In one embodiment, the attachment mechanism includes a screw connection mechanism. In one embodiment, the first hollow cylinder further includes a central axis, the second hollow cylinder further includes a central axis, the tube further includes a central axis and the piston further includes a central axis, wherein the central axis of the first hollow cylinder is coaxially disposed with the central axis of the second hollow cylinder, the central axis of the tube and the piston. In one embodiment, the second diameter is greater than the first diameter. In one embodiment, the second hollow cylinder further includes a central axis, wherein the communication is further configured to occur across substantially the entire cross-sectional area of the second hollow cylinder and the cross-sectional area is disposed at right angle to the central axis of the second hollow cylinder. In one embodiment, the first hollow cylinder further includes a central axis, the syringe further includes a safety shield configured to be slidable along a path parallel to the central axis of the first hollow cylinder from a first unlocked position to a second locked position disposed in a manner to shield a needle disposed on the first end of the first hollow cylinder from contact with a user. In one embodiment, the first substance includes a liquid and the second substance includes a solid.

In accordance with the present invention, there is further provided a syringe including:
(a) a first hollow cylinder including a first end, a second end and a first inner diameter;
(b) a second hollow cylinder including a first end, a second end, a second inner diameter and a central axis;
(c) a tube including a first end having the first inner diameter and a second end having the second inner diameter, wherein the tube is configured to connect the first hollow cylinder at the second end of the first hollow cylinder and the second hollow cylinder at the first end of the second hollow cylinder and the second inner diameter is greater than the first inner diameter; and
(d) a piston configured to slide within the first hollow cylinder, the tube and the second hollow cylinder, a first position of the piston within the first hollow cylinder defining a first space between the piston and the first end of the first hollow cylinder and a second space between the piston and the second end of the second hollow cylinder, wherein the first space is isolated from the second space, wherein a communication of a first substance within the first space and a second substance within the second space is enabled through the tube by withdrawing the piston from the first space and the communication is configured to occur across substantially the entire cross-sectional area of the second hollow cylinder and the cross-sectional area is disposed at right angle to the central axis of the second hollow cylinder.

In accordance with the present invention, there is further provided a method for mixing a first substance of a first chamber and a second substance of a second chamber, wherein communication of the first chamber and the second chamber is blocked by a removable member, the method including:
(a) positioning the first chamber at an elevation higher than the second chamber;

(b) removing the removable member to enable communication of the first substance with the second substance to form a mixture;
(c) positioning the second chamber at an elevation higher than the first chamber; and
(d) replacing the removable member to confine the mixture in the first chamber.

In one embodiment, the method further includes a step of agitating the mixture between step (b) and step (c). In one embodiment, the first substance includes a liquid and the second substance includes a solid. In one embodiment, the removing step further includes an action applied along a first axis and the replacing step further includes an action applied along a second axis and the first axis is disposed coaxially with the second axis.

An object of the present invention is to provide a syringe where two ingredients or components of an injectable material can be mixed just prior to its administration to keep the injectable material fresh.

Another object of the present invention is to provide a syringe configured to administer an injectable material composed of two components capable to be stored separately until an administration of the injectable material.

Another object of the present invention is to provide a syringe where two components of an injectable material can be mixed easily and thoroughly just prior to its administration keep the injectable material fresh.

Another object of the present invention is to provide a syringe composed essentially of the storage structures of the two components that form the injectable material that is prepared just in time for use.

Whereas there may be many embodiments of the present invention, each embodiment may meet one or more of the foregoing recited objects in any combination. It is not intended that each embodiment will necessarily meet each objective. Thus, having broadly outlined the more important features of the present invention in order that the detailed description thereof may be better understood, and that the present contribution to the art may be better appreciated, there are, of course, additional features of the present invention that will be described herein and will form a part of the subject matter of this specification.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 4 is a longitudinal view of one embodiment according to a present syringe in a post-administration condition.

FIG. 5 is a longitudinal cross-sectional view of the embodiment of a present syringe of FIG. 4 as taken along line B-B of FIG. 4.

FIG. 8 is a longitudinal view of one embodiment according to a present syringe in a pre-administration condition.

FIG. 9 is a longitudinal cross-sectional view of the embodiment of a present syringe of FIG. 8 as taken along line C-C of FIG. 8.

FIGS. 14-18 is a series of diagrams depicting an order in which a present syringe can be used to administer an injectable material.

PARTS LIST

Figure 1:
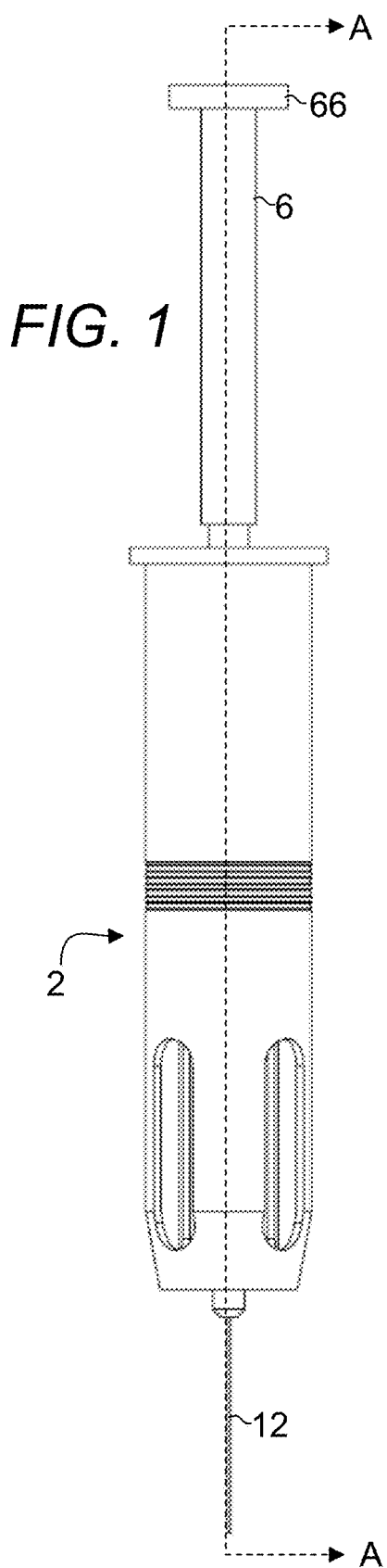
FIG. 1 is a longitudinal view of one embodiment according to a present syringe in a pre-administration condition.

2—syringe
4—piston
6—rod or plunger
8—chamber or space for holding first component
10—chamber or space for holding second component
12—hypodermic needle or cannula
14—first component, ingredient or substance, e.g., a liquid pharmaceutical
16—second component, ingredient or substance, e.g., a solid pharmaceutical
18—first hollow cylinder
20—second hollow cylinder
22—tube
24—stopper
26—portion of stopper
28—grasping point for stopper
30—pin
32—screw thread groove or track
34—bushing
36—cap
38—threaded receptacle
40—cap
42—threaded receptable
43—screw thread
44—cap including a threaded receptacle
46—transition angle
48—safety shield
50—screw
52—ring
54—opening
56—limiter
58—cup
60—protruding ring
62—groove
64—central axis of syringe
66—flange
68—tongue
70—groove
72—filler tube
74—first inner diameter
76—second inner diameter
78—skirt
80—recess
82—space between two engaged portions of a stopper
84—barrel
86—direction
88—direction
90—seal
92—sleeve
94—seal
96—first part
98—second part

PARTICULAR ADVANTAGES OF THE INVENTION

In use, the present syringe requires a pull-back of the rod of a piston to expose a first component to a second component. As the first component is held in a first storage space that expands into a space previously taken by a piston as the piston is pulled back, this creates a vacuum that results in an in-rush of slightly compressed air from the shrinking second storage space, causing the first component, a liquid, to scatter violently while also under the influence of gravity to mix with the second component, e.g., a powder, to aid in initiating mixing of the first and second components.

The present syringe does not require a forward (or compression) motion of a syringe in which two components are held for the two components to communicate with one another. As such, a user of the syringe does not need to guess the amount of force required to cause the communication. Communication of the two components can occur when the rod is pulled back until it can be no longer be retracted. In an embodiment in which a stopper is used, the action useful for dismantling the stopper also causes the rod to be pulled back to enable communication of the two components. The stopper further eliminates the risk of accidental reconstitution due to vibrations caused during transportation.

The present syringe includes a sufficiently large mixing chamber that includes not only the storage space of a first component, the storage space of a second component but also the space vacated by the piston and rod of the syringe.

The present syringe includes assemblies that can be combined to form a functional syringe. A first assembly of the syringe is useful for holding a first component and a second assembly of the syringe is useful for holding a second component. As the assemblies are available separately, they can be stored at two different locations or ambient conditions until they become necessary to be combined. Further, the present syringe allows healthcare workers to immediately prepare the products at the time of administration, decreasing post-reconstituted waste.

The present syringe decreases the time and steps that reconstituted vaccines and medications require, allowing healthcare workers to be utilized in a more efficient manner. Also, the present syringe reduces raw material wastes, e.g., glass vials and plastic caps, etc. The present syringe offers limited opportunities for error when compared to traditional disposable syringes as a stopper is provided in the present syringe to both prevent accidental administration of an injection of a material that has not been mixed. The removal of the stopper automatically causes a material to be reconstituted.

DETAILED DESCRIPTION OF A PREFERRED EMBODIMENT

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

Figure 2:
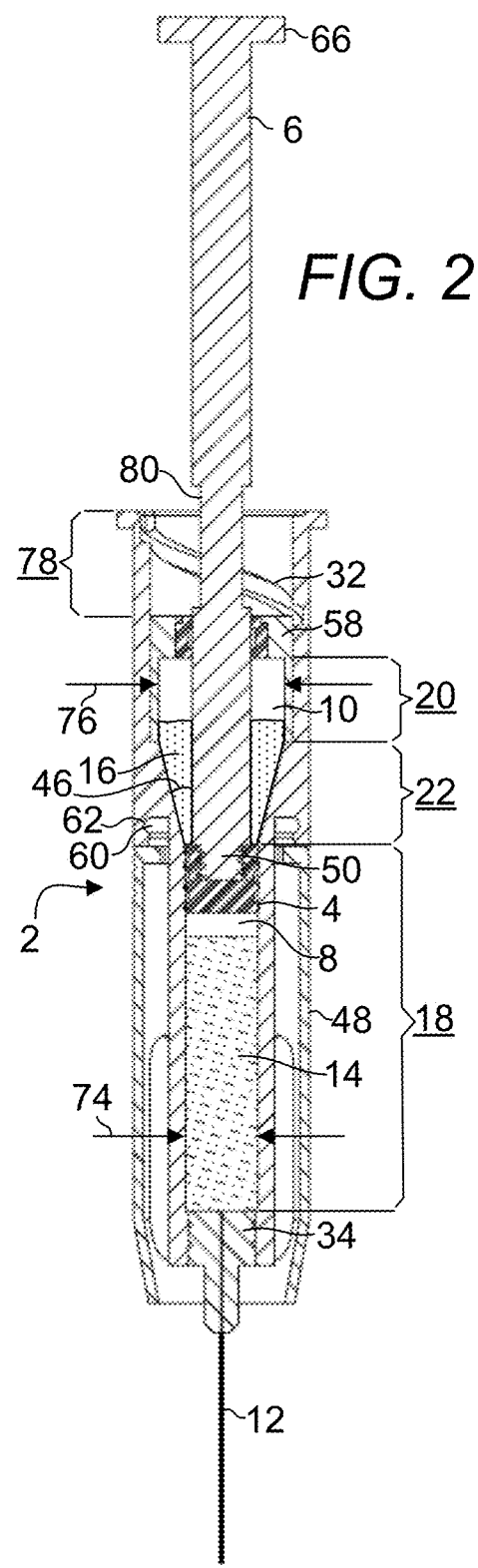
FIG. 2 is a longitudinal cross-sectional view of the embodiment of a present syringe of FIG. 1 as taken along line A-A of FIG. 1.
Figure 3:
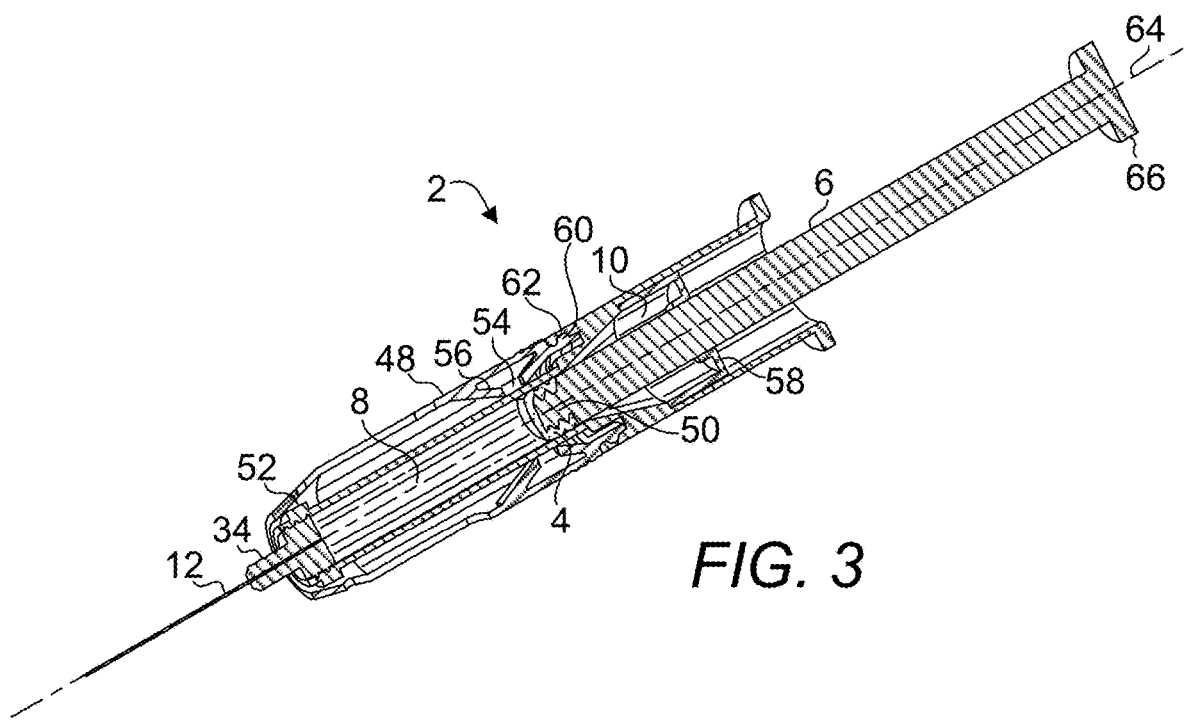
FIG. 3 is a front longitudinal cross-sectional view of the embodiment of a present syringe of FIG. 1 as taken along line A-A of FIG. 1.

FIG. 1 is a longitudinal view of one embodiment according to a present syringe 2 in a pre-administration condition. FIG. 2 is a longitudinal cross-sectional view of the embodiment of a present syringe 2 of FIG. 1 as taken along line A-A of FIG. 1. FIG. 3 is a front longitudinal cross-sectional view of the embodiment of a present syringe 2 of FIG. 1 as taken along line A-A of FIG. 1. The syringe 2 includes a first hollow cylinder 18, a second hollow cylinder 20, a tube 22, e.g., a frustum, and a piston 4. The first hollow cylinder 18 includes a first end, a second end and a first inner diameter 74. The second hollow cylinder 20 includes a first end, a second end and a second inner diameter 76, wherein the second end of the second hollow cylinder 20 is fixed with respect to the first end of the second hollow cylinder 20. In other words, the distance between the first end of the first hollow cylinder 18 and the second end of the second hollow cylinder 20 does not change. The tube 22 includes a first end having the first inner diameter 74 and a second end having the second inner diameter 76, wherein the tube 22 is configured to connect the first hollow cylinder 18 at the second end of the first hollow cylinder 18 and the second hollow cylinder 20 at the first end of the second hollow cylinder 20. In one embodiment, the tube 22 extends outwardly at a transition angle 46 of about 10 to about 80 degrees in a direction from the first hollow cylinder to the second hollow cylinder. In the embodiment shown in FIG. 2, the first and second hollow cylinders 18, 20 and the tube 22 are constructed as a single unit. In another embodiment disclosed elsewhere herein, the first hollow cylinder 18 is made separately available from the second hollow cylinder 20 and the tube 22. The piston 4 is configured to slide within the first hollow cylinder 18 and through the tube 22 and the second hollow cylinder 20. While disposed in a first position of the piston 4 within the first hollow cylinder 18, the piston 4 isolates the lumens of all three hollow cylinders into two spaces, i.e., a first space 8 between the piston 4 and the first end of the first hollow cylinder 18 and a second space 10 between the piston 4 and the second end of the second hollow cylinder 20. It shall be noted that the piston 4, first hollow cylinder 18, second hollow cylinder 20 and tube 22 are all coaxially disposed with the central axis of the syringe 2, i.e., the central axis of the piston 4, the central axis of the first hollow cylinder 18, the central axis of the second hollow cylinder 20 and the central axis of the tube 22 coincide with one another. It shall also be noted that the second diameter 76 is greater than the first diameter to allow the contents of the first hollow cylinder 18 to flow into the second hollow cylinder 20 unimpeded once communication between the two spaces 8, 10 has been enabled or established.

There is further provided a safety mechanism to prevent exposure of a user to the needle 12. Referring to FIGS. 1-3, a safety shield 48 is shown disposed in an undeployed position as the syringe 2 has yet to be used and therefore a patient shall be exposed to the needle 12 to receive an injection. The safety shield 48 includes a protruding ring 60 disposed on one end of the safety shield 48, the protruding ring 60 configured to be removably coupled to a groove 62 integrally built with the tube 22.

A communication of a first substance within the first space 8 and a second substance within the second space 10 is enabled through the tube 22 by an act of withdrawing the piston 4 from the first space 8 and the communication is configured to occur in a total volume of at least a combined volume of the first space 8 and the second space 10 as shown in FIG. 17. In the embodiments shown throughout, the piston 4 is connected to a rod 6 configured to be slideable through an opening at the second end of the second hollow cylinder 20. One end of the rod 6 is terminated with a screw 50 configured to receive a piston 4 while the other end of the rod 6 is terminated with a thumb engageable flange 66. The piston 4 may alternatively be constructed as a single unit with the rod 6 provided that the piston 4 is capable of sealing the first space 8 from the second space 10. In one example, the piston 4 is constructed from a polymeric material, e.g., rubber, etc., an elastomeric material sufficiently resilient yet sufficiently rigid to seal the first space 8 from the second space 10 while it is disposed partially or in its entirety at the second end of the first hollow cylinder 8.

The syringe further includes a needle for delivering at least one of the first substance and a mixture of the first substance and the second substance where the needle 12 is disposed on the first end of the first hollow cylinder 18. The first substance 14 may include a liquid and the second substance 16 may include a solid, e.g., a powder. In another embodiment, both the first and second substances may include a liquid. In yet another embodiment, the first substance may be a gas and the second substance may be a liquid or solid. If one of the two substances is a solid, the solid is preferably stored in the second space 10 to promote mixing and lessen the opportunity that an undissolved or poorly dissolved solid can be found clogging the needle 12.

As the inner diameter of the tube 22 expands from a first end of the tube 22 to the second end of the tube 22 and the diameter of the rod 6 is no larger than the diameter of the piston 4, a retraction of the rod 6 away from the first hollow cylinder 18 enables a path for the first substance 14 to be mixed with the second substance 16. The syringe 2 can be accidentally or intentionally misused without a means for immobilizing the rod 6 with respect to the first hollow cylinder 18 against a squeezing action applied to the syringe 2. A user who is under the influence of the ubiquitous act of depressing a rod or plunger to cause an inward stroke to expel a substance from the tip of a syringe, may proceed to do so without having mixed the two components contained within the syringe before use, potentially requiring the syringe to be discarded and causing harm to the recipient of an injection of an ineffective substance due to the lack of mixing with a complementary substance. In preventing an inadvertent depression of the syringe, a stopper that is easily removable, is provided. FIGS. 1-3 are shown without a stopper.

Figure 6:
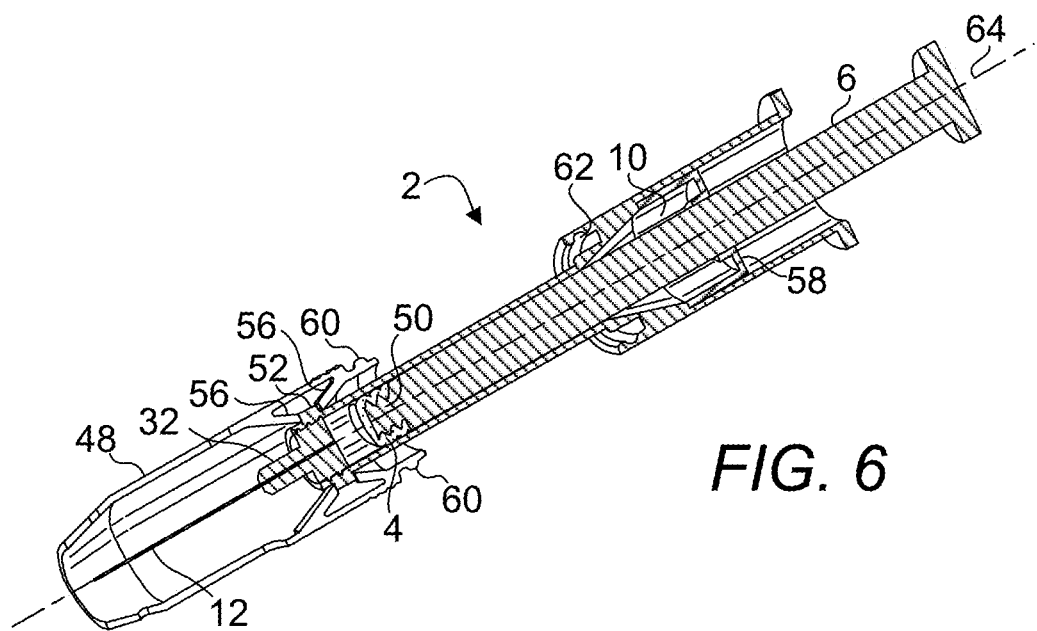
FIG. 6 is a front longitudinal cross-sectional view of the embodiment of a present syringe of FIG. 4 as taken along line B-B of FIG. 4.
Figure 7:
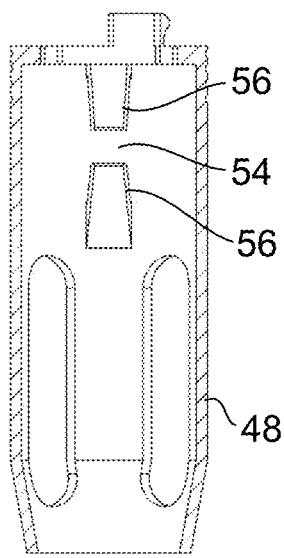
FIG. 7 is a cross-sectional view of a safety shield, depicting a limiter useful for immobilizing the safety shield with respect other parts of a present syringe upon a ring of the syringe becoming lodged in an opening of the limiter.

FIG. 4 is a longitudinal view of one embodiment according to a present syringe 2 in a post-administration condition. FIG. 5 is a longitudinal cross-sectional view of the embodiment of a present syringe 2 of FIG. 4 as taken along line B-B of FIG. 4. FIG. 6 is a front longitudinal cross-sectional view of the embodiment of a present syringe 2 of FIG. 4 as taken along line B-B of FIG. 4. FIG. 7 is a cross-sectional view of a safety shield, depicting a limiter useful for immobilizing the safety shield with respect other parts of a present syringe 2 upon a ring 60 of the syringe becoming lodged in an opening 54 of the limiter 56. Here, the piston 4 is shown to assume a position that leaves no space between the piston 4 and the needle 12 as a mixture previously held in the syringe has been expelled through needle 12, e.g., via an injection into a patient. It shall also be noted that the safety shield 48 is now disposed in its erected position, shielding a user as well as a patient from an accidental contact with the needle 12. In deploying the safety shield 48, a user simply grasps before pulling the safety shield 48 forwardly towards the needle 12 until ring 52 becomes lodged in an opening 54 of the limiter 56. The safety shield 48 is preferably constructed from a sufficiently resilient material such that a sufficiently large pulling force causes deformation of the safety shield 48 to detach the protruding ring 60 from the groove 62 to allow the limiter 56 to be disposed in a position to be coupled with ring 52 to secure the safety shield 48 in place to avoid contact of the needle 12 with a user or patient. Upon deploying the safety shield 48, the syringe can now be safely discarded.

Figure 10:
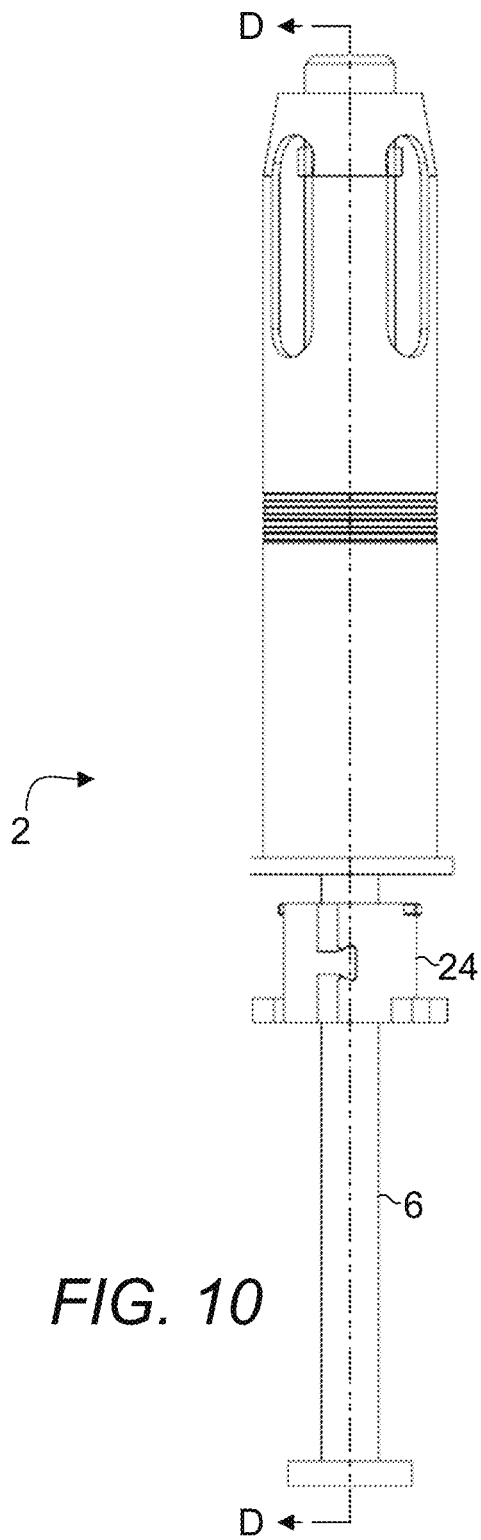
FIG. 10 is a longitudinal view of one embodiment according to a present syringe in a pre-administration condition.
Figure 11:
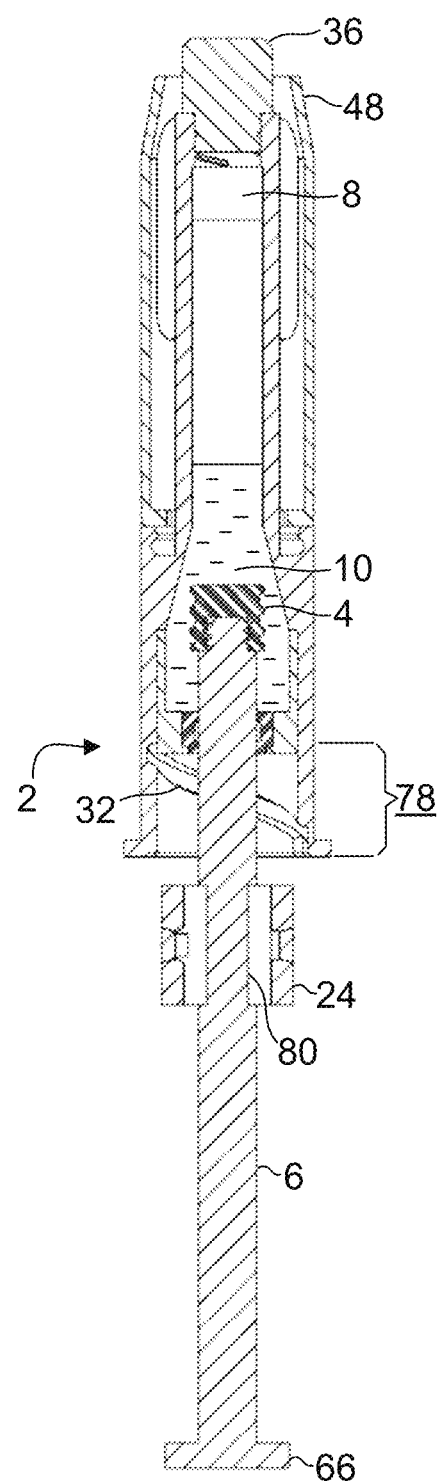
FIG. 11 is a longitudinal cross-sectional view of the embodiment of a present syringe of FIG. 10 as taken along line D-D of FIG. 10.
Figure 12:
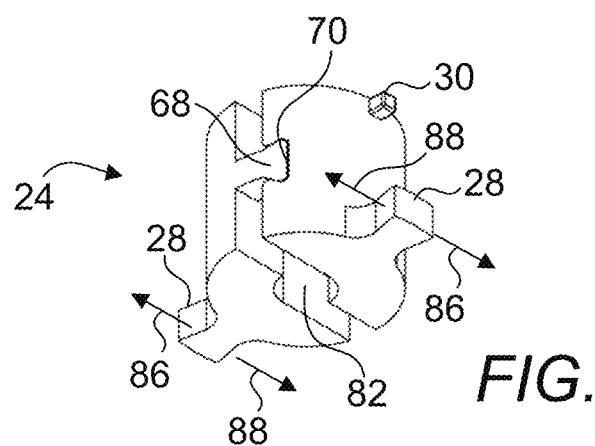
FIG. 12 is a bottom perspective view of a stopper of a present syringe with the two portions of the stopper attached to one another.
Figure 13:
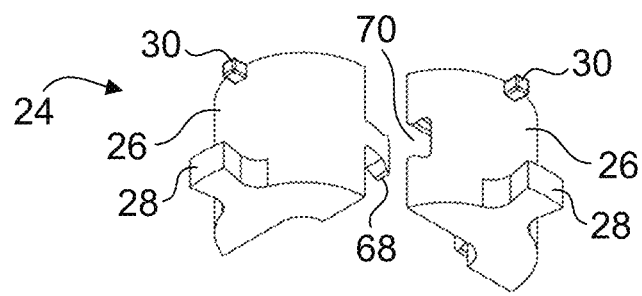
FIG. 13 is a bottom perspective view of a stopper of a present syringe with the two portions of the stopper detached from one another.

FIG. 8 is a longitudinal view of one embodiment according to a present syringe 2 in a pre-administration condition. FIG. 9 is a longitudinal cross-sectional view of the embodiment of a present syringe 2 of FIG. 8 as taken along line C-C of FIG. 8. FIG. 10 is a longitudinal view of one embodiment according to a present syringe 2 in a pre-administration condition. FIG. 11 is a longitudinal cross-sectional view of the embodiment of a present syringe 2 of FIG. 10 as taken along line D-D of FIG. 10. FIG. 12 is a bottom perspective view of a stopper of a present syringe 2 with the two portions 26 of the stopper 24 attached to one another. FIG. 13 is a bottom perspective view of a stopper 24 of a present syringe 2 with the two portions 26 of the stopper 24 detached from one another. Here, a stopper 24 is utilized to prevent improper use of the syringe 2. Note that a portion of the rod 6 is recessed at a recess 80 to accommodate the stopper 24. A skirt 78 is configured to extend from the second end of the second hollow cylinder 20 to both provide a shroud to contain the stopper 24 and to provide tracks 32 along which the stopper 24 can be screwed into a secure position within the shroud to be seated. Two pins 30 are disposed substantially on a first end of the stopper 24 while two grasping points 28 are disposed substantially on a second end of the stopper 24. Each grasping point 28 is essentially a diametrically-extending protrusion that a user can easily grasp with one or more fingers to apply a twisting force thereto in either direction 86 or direction 88. In coupling the stopper 24 to the syringe 2, two halves 26 of the stopper 24 are brought around the recess 80 and arranged such that a tongue 68 of one is aligned with a groove 70 of the other before the halves 26 are clamped onto the recess 80 to result in an arrangement where the two pins 30 and the two grasping points 28 are opposingly disposed about the central axis of the rod 6 and a space between two engaged halves 26. The stopper 24, now clamped onto rod 6, is then disposed so that the pins 30 are each aligned with one of the tracks 32 disposed on an inner wall of the skirt 78 before the stopper is seated in the skirt 78 following a twisting motion in a first direction 86 that advances the stopper 24 until the second end of stopper 24 coincides with the end of the skirt 78 away from the second hollow cylinder 20, leaving the grasping points 28 exposed. In one embodiment, the stopper 24 requires about 0.1 to about 2 turns to be unseated from its fully seated position. In one embodiment, the pitch of the grooves or tracks 32 is about 35 mm per revolution. This translates to about 14 mm in linear motion along the central axis of the second hollow cylinder 20 per 0.4 turn of the stopper 24 about the central axis of the second hollow cylinder 20. While seated within the skirt 78, a pull of the rod 6 with respect to the cylinders 18, 20, 22 will be met with sufficient resistance that immobilizes the rod 6. In order to remove the stopper 24 to allow an administration of an injection, a user first grasps the grasping points 28 before twisting the stopper 24 about the central axis of the rod 6 in a second direction 88 that is opposite of the first direction. In addition to exposing the stopper 24, upon clearing the skirt 78 so that the stopper 24 can disintegrate into the halves 26 and subsequently removed and discarded, such action also withdraws the rod 6. In one embodiment, such action also withdraws the rod 6 sufficiently to allow communication of the first substance and the second substance. Therefore, in this embodiment, in addition to serving as a means to prevent misuse of the syringe, the stopper 24 forces the user to use the syringe 2 in a manner intended, i.e., by forcing the user to allow mixing of the substances provided in the syringe 2 before the syringe 2 can be used.

Figure 14:
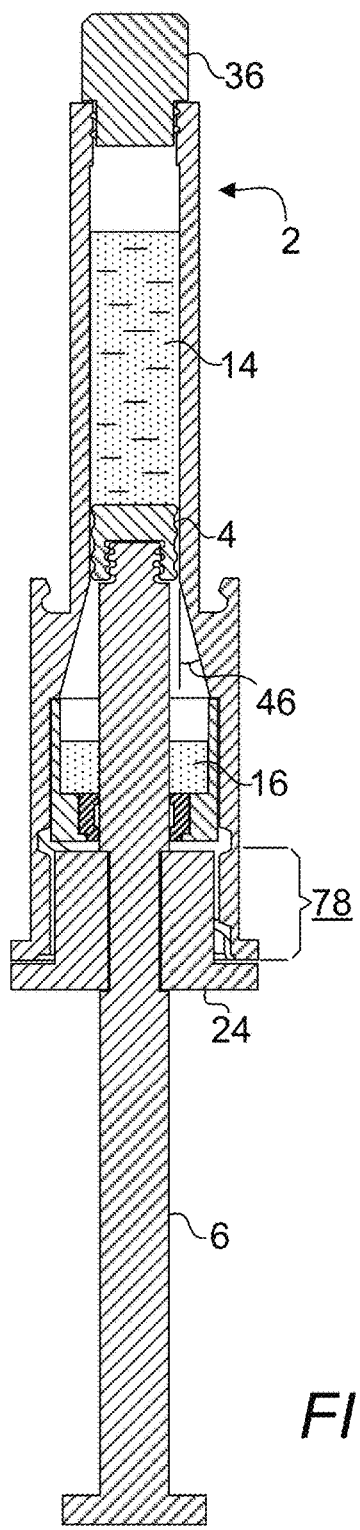
Figure 15:
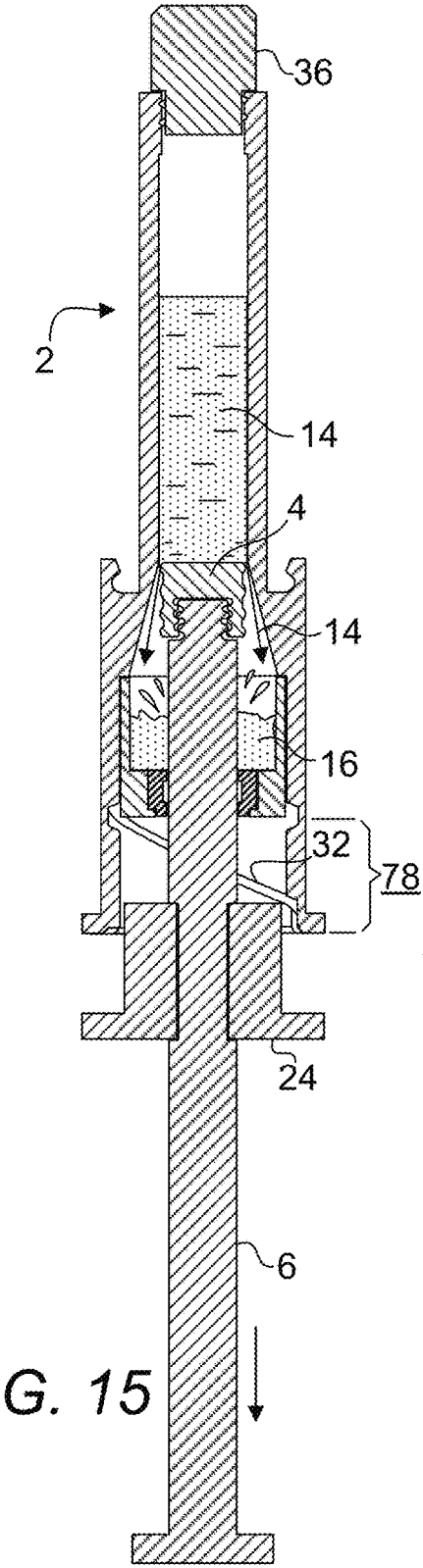
Figure 16:
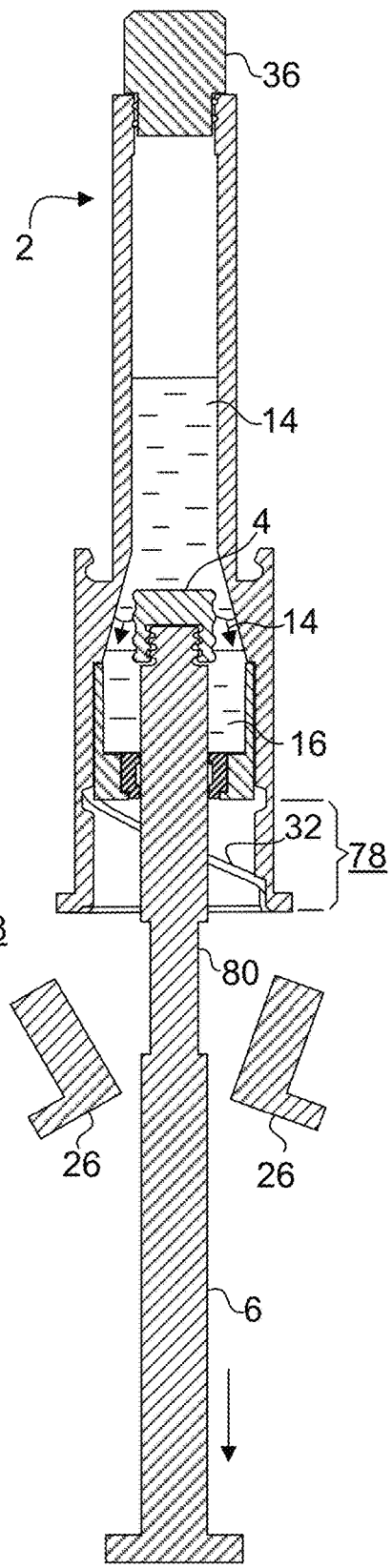

FIGS. 14-18 is a series of diagrams depicting an order in which a present syringe 2 can be used to administer an injectable material. The syringe 2 is pre-filled with an injectable material composed of two separate components 14, 16. If the injectable material is a mixture of a liquid and a solid, the liquid is preferably disposed in the first space 8, i.e., the space adjacent a needle 12. Disclosed herein is a method for mixing a first substance of a first space 8 and a second substance of a second space 10, wherein communication of the first space and the second space is blocked by a removable member, e.g., a piston 4. First, the syringe is orientated such that the first space 8 is disposed at an elevation higher than the second space 10 as shown in FIG. 14. In other words, the syringe 2 is held such that the needle 12 is pointed upwardly. This is followed by removing the piston 4 to enable communication of the first substance 14 with the second substance 16 to form a mixture as shown in FIGS. 15 and 16. Referring to FIG. 15, as the first component is held in a first storage space that expands into a space previously taken by a piston 4 as the piston 4 is pulled back, this creates a vacuum that results in an in-rush of slightly compressed air from the shrinking second storage space, causing the first component 14, a liquid, to scatter violently while also under the influence of gravity to mix with the second component 16, e.g., a powder, to aid in initiating mixing of the first and second components. As the rod 6 continues to be withdrawn as shown in FIG. 16, the stopper 24 eventually clears the skirt 78 and falls out as it disintegrates into its halves 26 as the tongue 68 of a half disengages from the groove 70 of another and the first substance continues to mix with the second substance. It shall be noted that upon full retraction of rod 6 as shown in FIG. 17, the first space 8 is no longer partially occupied by the piston 4 and the second space 10 is no longer partially occupied by a portion of rod 6, resulting in the maximum total space or "mixing chamber" for mixing. The mixing chamber now includes the volume occupied by the first space 8 and the second space 10 without including the volume taken up by the piston 4. It shall be noted that, in this configuration, the communication is configured to occur across substantially the entire longitudinal cross-sectional area of the second hollow cylinder where the cross-sectional area is disposed at right angle to a central axis of the second hollow cylinder 20. When mixing has been considered satisfactory, the syringe 2 is flipped over, i.e., by positioning the second space 10 at an elevation higher than the first space 8 until the mixture has drained into the first space 8 in its entirety before the rod 6 is advanced and before the piston 4 enters the lumen of the first hollow cylinder 18 to capture the entire volume of the mixture in the first hollow cylinder 18 to be injected in a patient. The total volume of the mixture is preferably equal to or less than the first space to avoid waste as any mixture not contained within the first space 8 is left behind in the syringe 2. The syringe 2 may simply be held in a position as shown in FIG. 17 for several seconds for the mixing of a liquid and a highly dissolvable solid or two liquids. For a solid with low dissolvability, the mixture is agitated in the syringe 2 while disposed in an orientation shown in FIG. 17 or in any other orientations. The syringe 2 is intuitively configured as both the action required to prepare the syringe 2 for an injection and the action required to administer the injection both rest on a common axis, i.e., the central axis 64 of the syringe 2. The present syringe 2 can alternatively be useful for administering a single substance. For an application where the contents of the second space is unnecessary or undesired, the syringe 2 can simply be used to provide only the contents pre-loaded in the first space 8.

Figure 19:
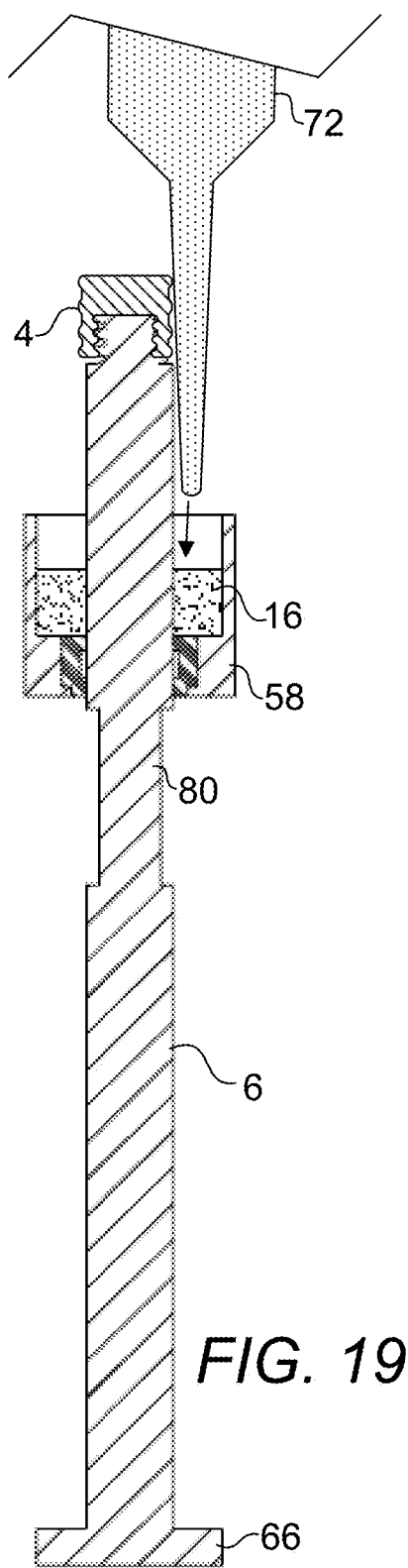
FIGS. 19-22 depict assemblies useful for constructing one embodiment of a present syringe such that an injectable mixture can be mixed therein prior to its use.
Figure 20:
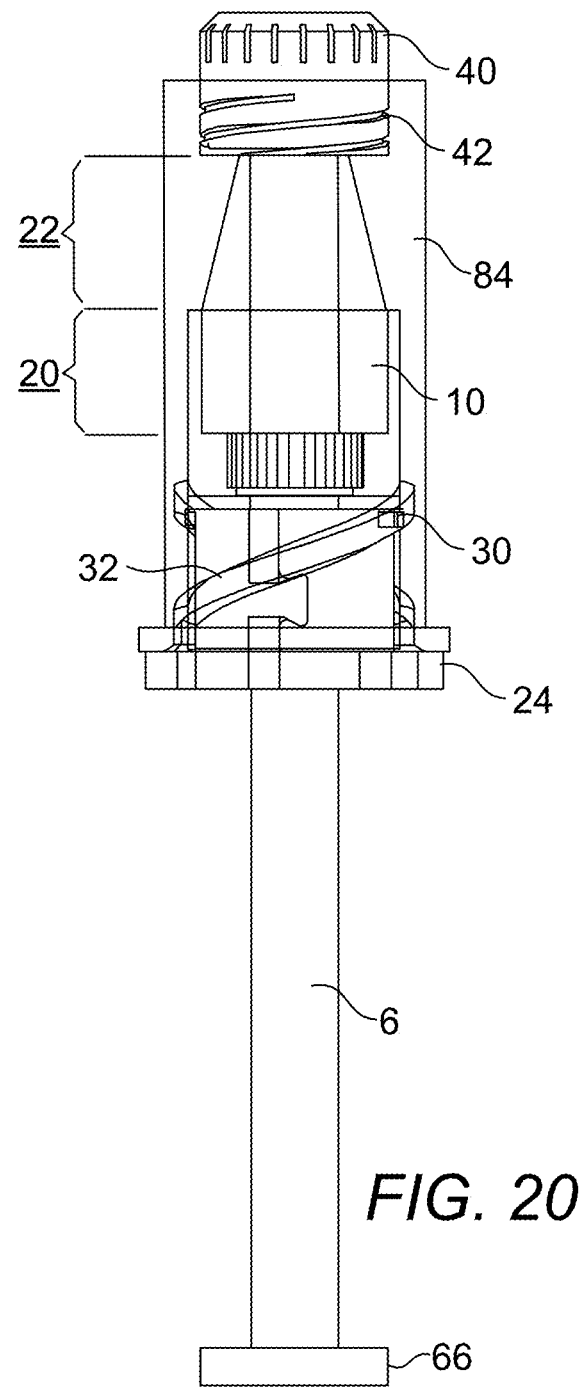
Figure 21:
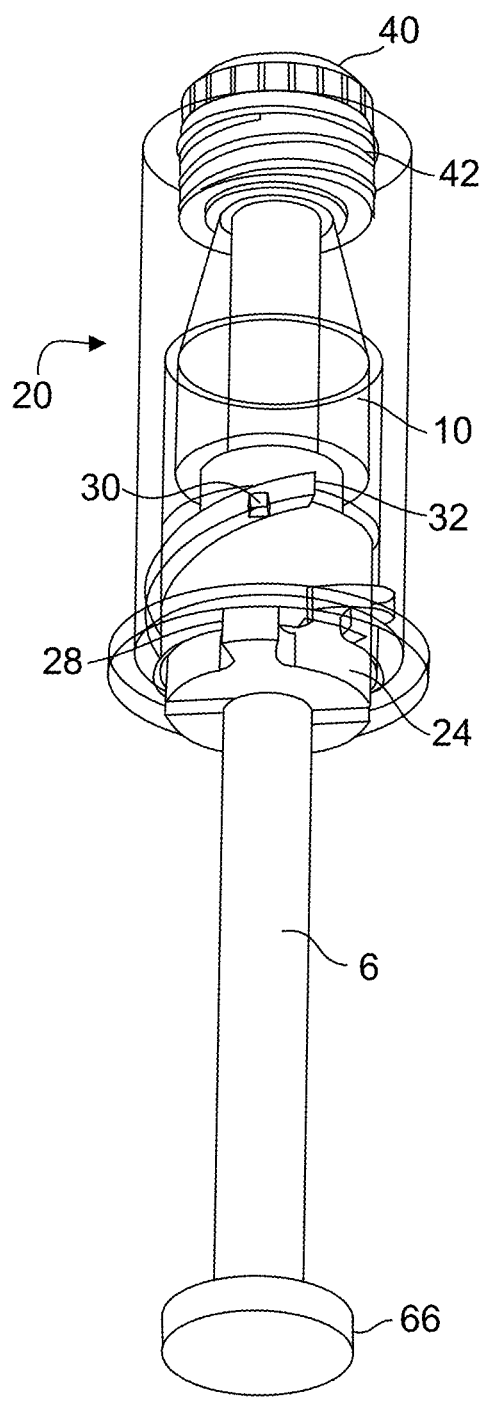
Figure 22:
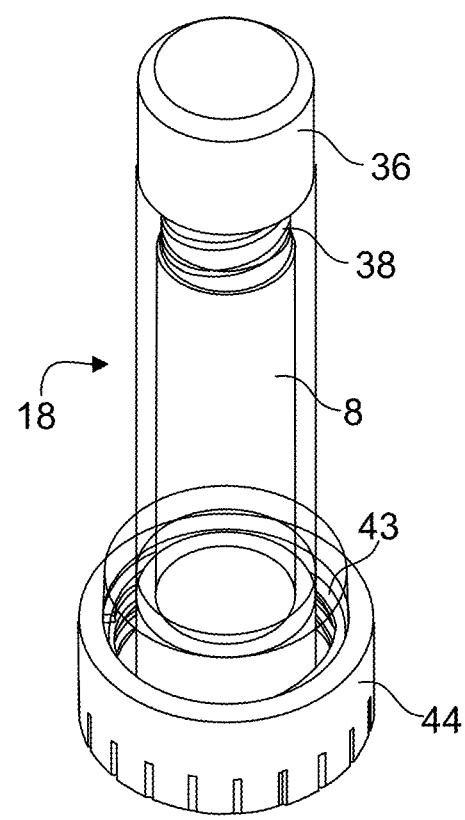
Figure 23:
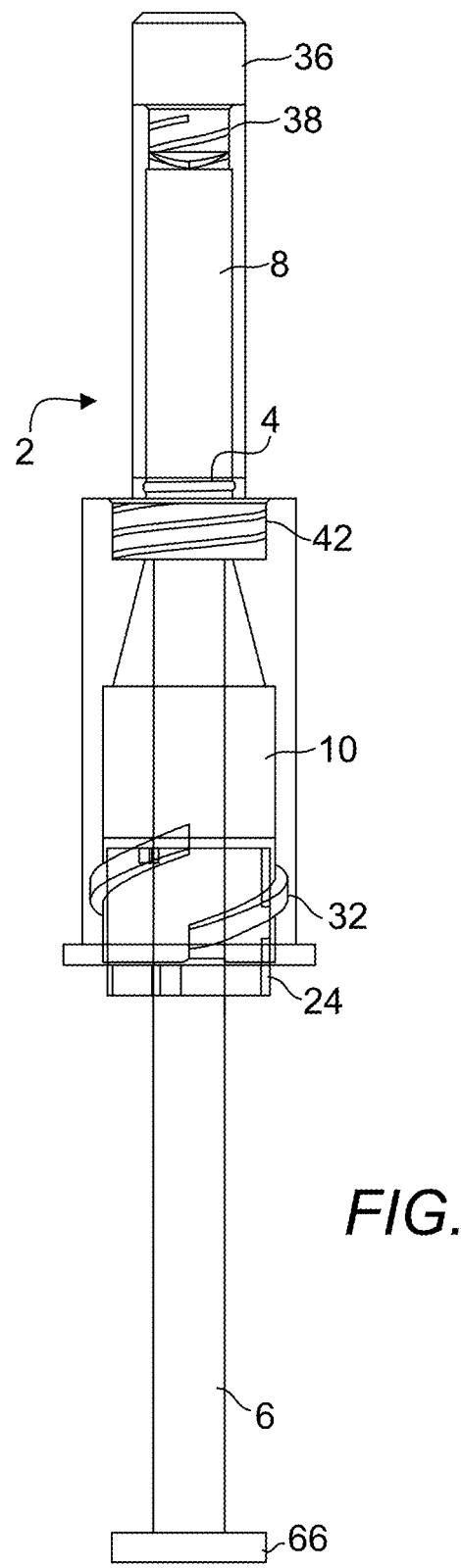
FIG. 23 depicts one embodiment of a present syringe constructed from parts disclosed in FIGS. 20-22.

FIGS. 19-22 depict assemblies useful for constructing one embodiment of a present syringe 2 such that an injectable mixture can be mixed therein prior to its use. Referring to FIG. 19, a cup 58 is provided with a rod 6 already inserted through an opening through the bottom of the cup 58. The cup 58 is filled with a second substance 16 through a filler tube 72 and the halves 28 are clamped around recess 80. Referring to FIGS. 20 and 21, the cup is then fixedly installed within a barrel 84, e.g., with an adhesive or by ultrasonic welding to essentially result in a second hollow cylinder 20 that is connected to a tube 22 and a piston disposed to block a lumen at a first end of the barrel 84. In the embodiment shown in FIGS. 20 and 21, a cap 40 is secured to the first end of the barrel 84 by means of a threaded receptacle 42 to protect the piston. FIG. 22 depicts a first hollow cylinder 18 that is capped at its first end with a cap 36 secured to the first hollow cylinder 18 with a screw thread and terminated at its second end with a screw thread 43 coupled with a threaded receptacle of a cap 44. To fill the first hollow cylinder 18, one of the caps 40, 44 is removed to receive a substance before the cap is replaced to seal the substance therein. FIG. 23 depicts one embodiment of a present syringe 2 constructed from assemblies disclosed in FIGS. 20-22. In doing so, the cap 40 of barrel 84 is removed to expose the threaded receptacle 42. The orientation at which the barrel 84 is held is inconsequential as space 10 is sealed at one end with the piston 4 and the other with the rod 6. The first hollow cylinder 18 is first held with the end of first hollow cylinder 18 capped with cap 44 pointed upwardly before the cap 44 is removed such that the substance contained therein remains. The exposed threaded receptacle 42 is then aligned with and coupled to screw thread 43 to form the syringe 2 depicted in FIG. 23. FIGS. 20 and 21 show an assembly that can be stored independently and separately from the assembly of FIG. 22. Therefore, the two substances of the syringe can be stored separately in two different locations and under two highly diverse ambient conditions. For instance, the assembly shown in FIG. 22 and hence the first substance stored therein, may be stored at a very low temperature while the assembly shown in FIGS. 20 and 21 and hence the second substance stored therein, may be stored at room temperature prior to the reconstitution of the second substance by adding the first substance. In one embodiment not shown, the assembly shown in FIG. 22 may also be secured to the assembly shown in FIGS. 20 and 21 by means of an adhesive, ultrasonic welding, etc., for a syringe having substances that may be disposed at the same ambient condition. Upon mixing, the mixture of the substances is ready to be injected. At this point, the cap 36 may be replaced with a needle supported on a bushing 34 as shown in FIG. 1 where the screw thread equipped bushing 34 is coupled with threaded receptacle 38. To fill a syringe where the first and second hollow cylinders 18, 20 and the tube 22 are constructed as a single unit, the process to fill the syringe 2 is similar to the process disclosed earlier, except for the lack of a need to first attach the first hollow cylinder to a barrel as the first hollow cylinder is already part of the barrel.

Figure 24:
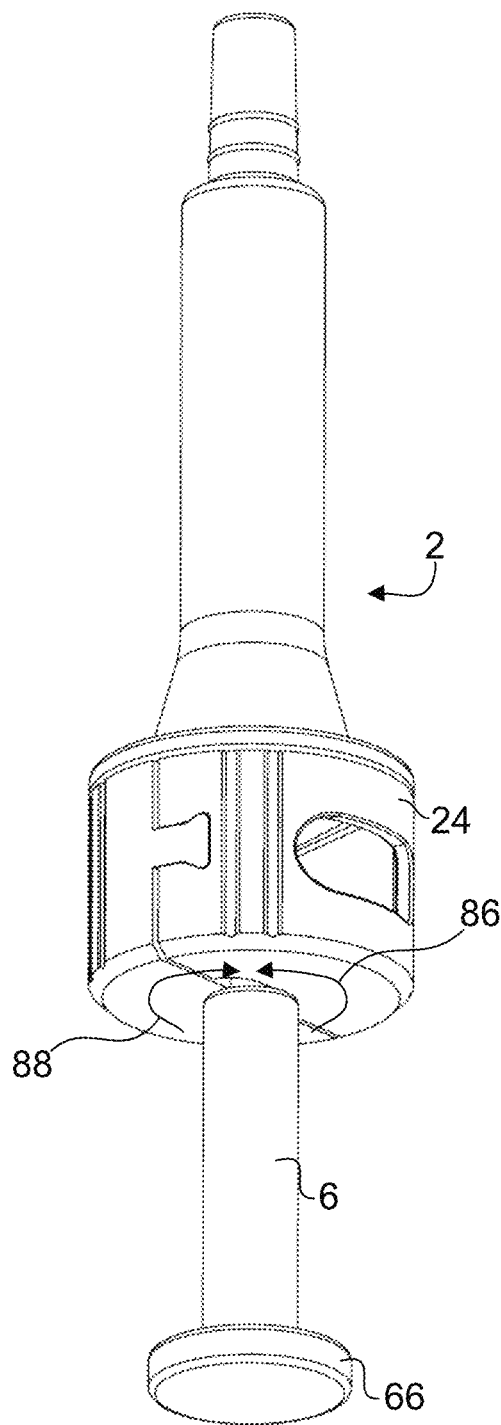
FIG. 24 is a rear longitudinal view of one embodiment according to a present syringe in a pre-administration condition.
Figure 25:
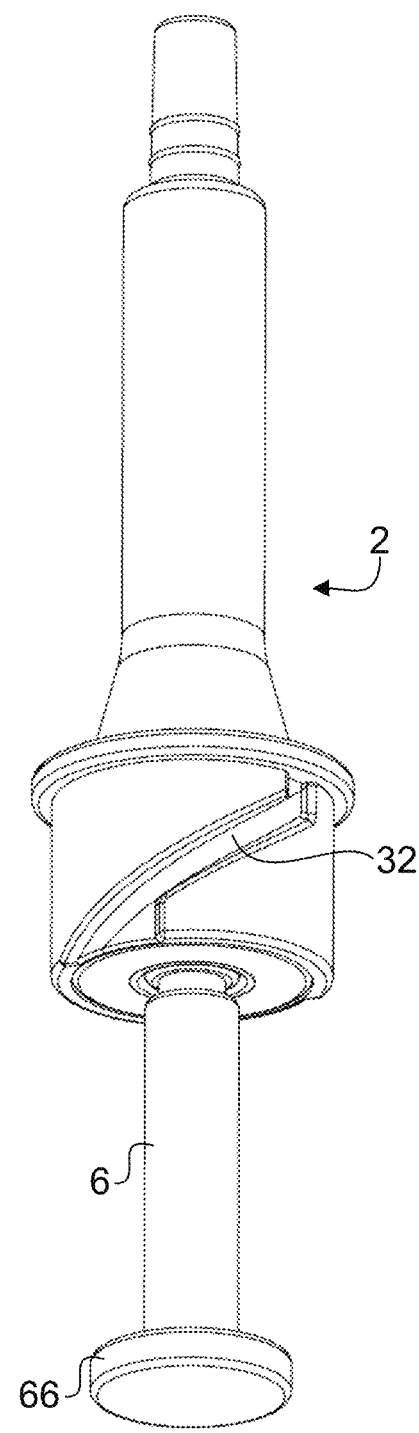
FIG. 25 is a rear longitudinal view of one embodiment according to a present syringe in a pre-administration condition of FIG. 24 with the stopper shown in FIG. 24 removed to reveal the second hollow cylinder.
Figure 26:
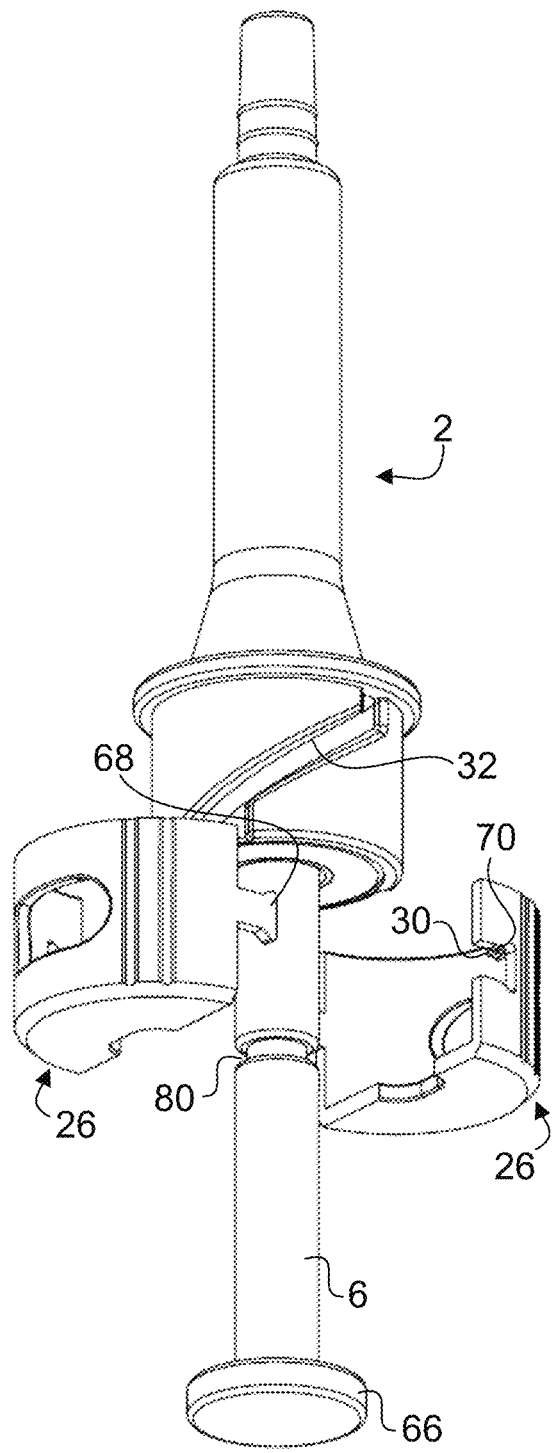
FIG. 26 is a rear longitudinal view of one embodiment according to a present syringe of FIG. 24 in a condition where the stopper has been operationally removed and the rod has been sufficiently withdrawn to cause communication between a first and a second component.
Figure 27:
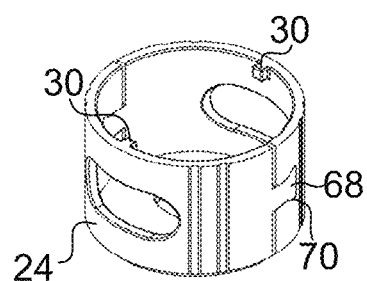
FIG. 27 is a top perspective view of a stopper of a present syringe with the two portions of the stopper attached to one another.
Figure 28:
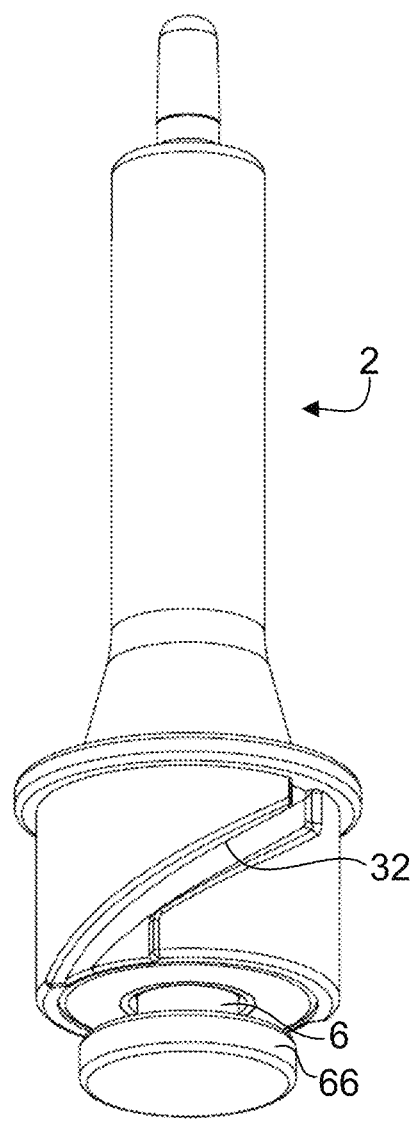
FIG. 28 is a rear longitudinal view of one embodiment according to a present syringe of FIG. 24 with its contents having been emptied.
Figure 29:
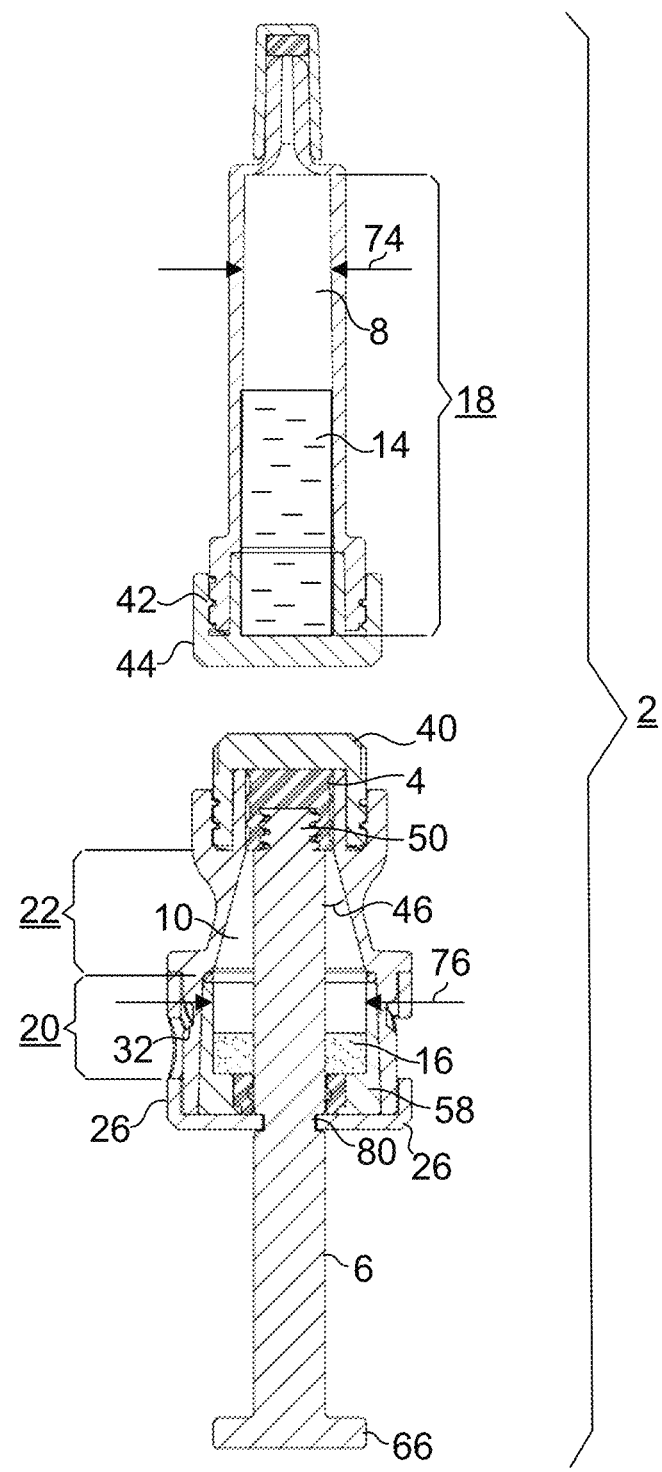
FIG. 29 is a longitudinal cross-sectional view of one embodiment according to a present syringe of FIG. 24 where the syringe is shown as two separate parts prior to being combined to form the syringe.

FIG. 24 is a rear longitudinal view of one embodiment according to a present syringe 2 in a pre-administration condition. FIG. 25 is a rear longitudinal view of one embodiment according to a present syringe 2 in a pre-administration condition of FIG. 24 with the stopper shown in FIG. 24 removed to reveal the second hollow cylinder. FIG. 26 is a rear longitudinal view of one embodiment according to a present syringe 2 of FIG. 24 in a condition where the stopper 24 has been operationally removed and the rod has been sufficiently withdrawn to cause communication between a first and a second component. FIG. 27 is a top perspective view of a stopper 24 of a present syringe with the two portions of the stopper attached to one another. FIG. 28 is a rear longitudinal view of one embodiment according to a present syringe 2 of FIG. 24 with its contents having been emptied. FIG. 29 is a longitudinal cross-sectional view of one embodiment according to a present syringe 2 of FIG. 24 where the syringe is shown as two separate parts prior to being combined to form the syringe 2. It shall be noted that the stopper 24 is configured to be removably coupled to the outer wall of the second hollow cylinder 20. In this embodiment, no skirt is required to contain a stopper, e.g., as in the embodiment shown in FIG. 9. Instead, screw thread grooves 32 are disposed on the outer wall of the second hollow cylinder 20. Referring to FIG. 27, two pins 30 are disposed substantially on a first end of the stopper 24. In coupling the stopper 24 to the syringe 2, two halves 26 of the stopper 24 are brought around a recess 80 and arranged such that a tongue 68 of one is aligned with a groove 70 of the other before the halves 26 are clamped onto the recess 80 to result in an arrangement where the two pins 30 are opposingly disposed about the central axis of the rod 6. The stopper 24, now clamped onto rod 6, is then disposed in a manner so that the pins 30 are each aligned with one of the two tracks 32 disposed on an outer wall of the second hollow cylinder 20 before the stopper 24 is seated around the second hollow cylinder 20 following a twisting motion in a first direction 86 that advances the stopper 24 until the second end of stopper 24 coincides with the second end of the second hollow cylinder 20 and the stopper 24 can no longer be advanced. While seated around the second hollow cylinder 20, a pull of the rod 6 with respect to the cylinders 18, 20, 22 will be met with sufficient resistance that immobilizes the rod 6. In order to remove the stopper 24 to allow an administration of an injection, a user first grasps the stopper 24 before twisting it about the central axis of the rod 6 in a second direction 88 that is opposite of the first direction. In one embodiment, the stopper 24 requires about 0.1 to about 2 turns to be unseated from its fully seated position. In one embodiment, the pitch of the grooves or tracks 32 is about 35 mm per revolution. This translates to about 14 mm in linear motion along the central axis of the second hollow cylinder 20 per 0.4 turn of the stopper 24 about the central axis of the second hollow cylinder 20. Upon clearing the tracks 32, the stopper 24 disintegrates into the halves 26 as the pins 30 are no longer confined in tracks 32. The halves 26 are subsequently removed and discarded. It shall be noted that the act of twisting the stopper 24 also withdraws the rod 6. In one embodiment, such action withdraws the rod 6 sufficiently to allow communication of the first substance and the second substance. Therefore again, in this embodiment, in addition to serving as a means to prevent misuse of the syringe, the stopper 24 forces the user to use the syringe 2 in a manner intended, i.e., by forcing the user to allow mixing of the substances provided in the syringe 2 before the syringe 2 can be used.

Figure 30:
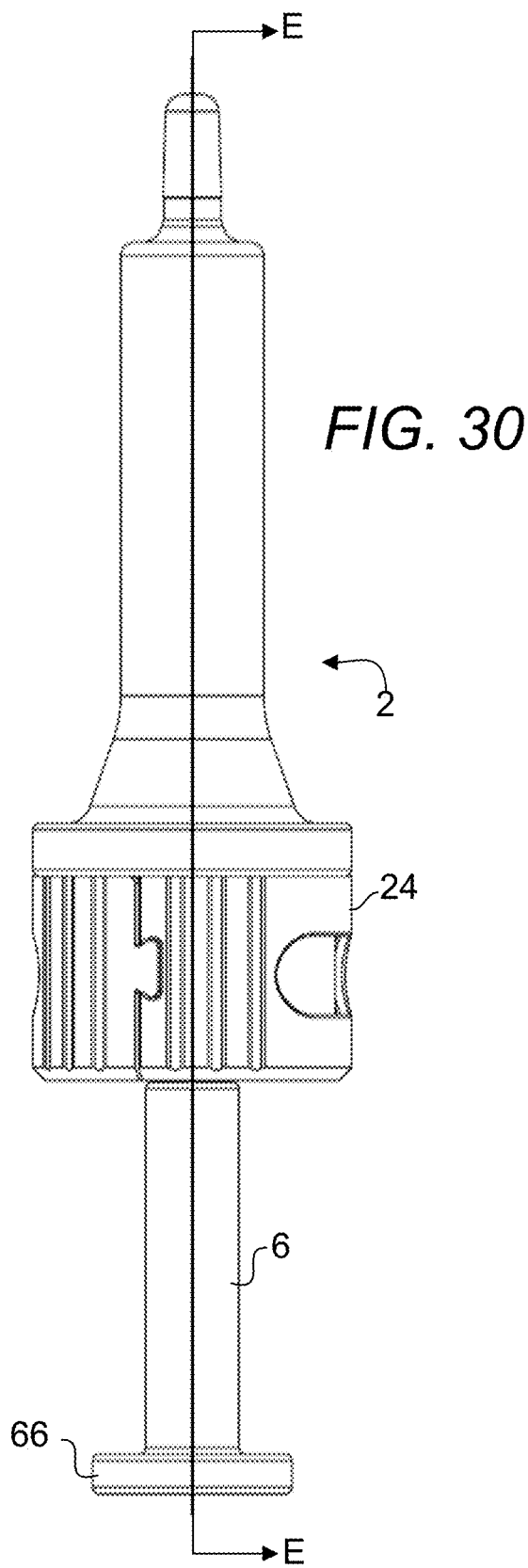
FIG. 30 is a longitudinal view of one embodiment according to a present syringe in a pre-administration condition.
Figure 31:
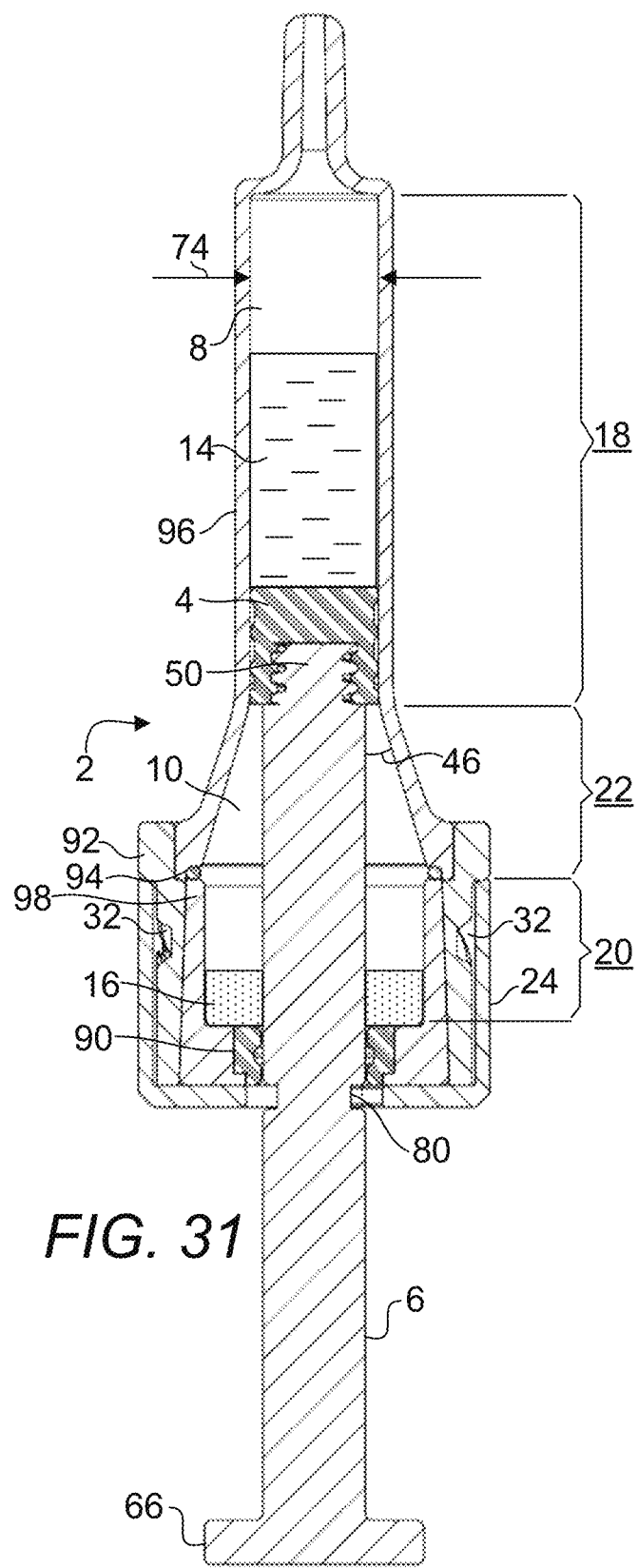
FIG. 31 is a longitudinal cross-sectional view of the embodiment of a present syringe of FIG. 30 as taken along line E-E of FIG. 30.

FIG. 30 is a longitudinal view of one embodiment according to a present syringe 2 in a pre-administration condition. FIG. 31 is a longitudinal cross-sectional view of the embodiment of a present syringe of FIG. 30 as taken along line E-E of FIG. 30. It shall be noted that the barrel of the syringe 2 is assembled from two parts, i.e., a first part 96 encompassing the first hollow cylinder 18 and the tube 22 and a second part 98 encompassing the second hollow cylinder 20 where the second part 98 is formed in the shape of a cup. In this embodiment, a seal 94, e.g., an O-ring is used between the first part 96 and the second part 98 to prevent leakage when the first part 96 and the second part 98 are assembled to form space 10. The screw thread grooves 32 are disposed on a sleeve 92 attached to the first part 96 and the second part 98, e.g., with an adhesive. Another seal 90 is provided to seal a gap between the second part and the rod 6. In one example, the first and second parts 96, 98 are both made from glass.

Figure 32:
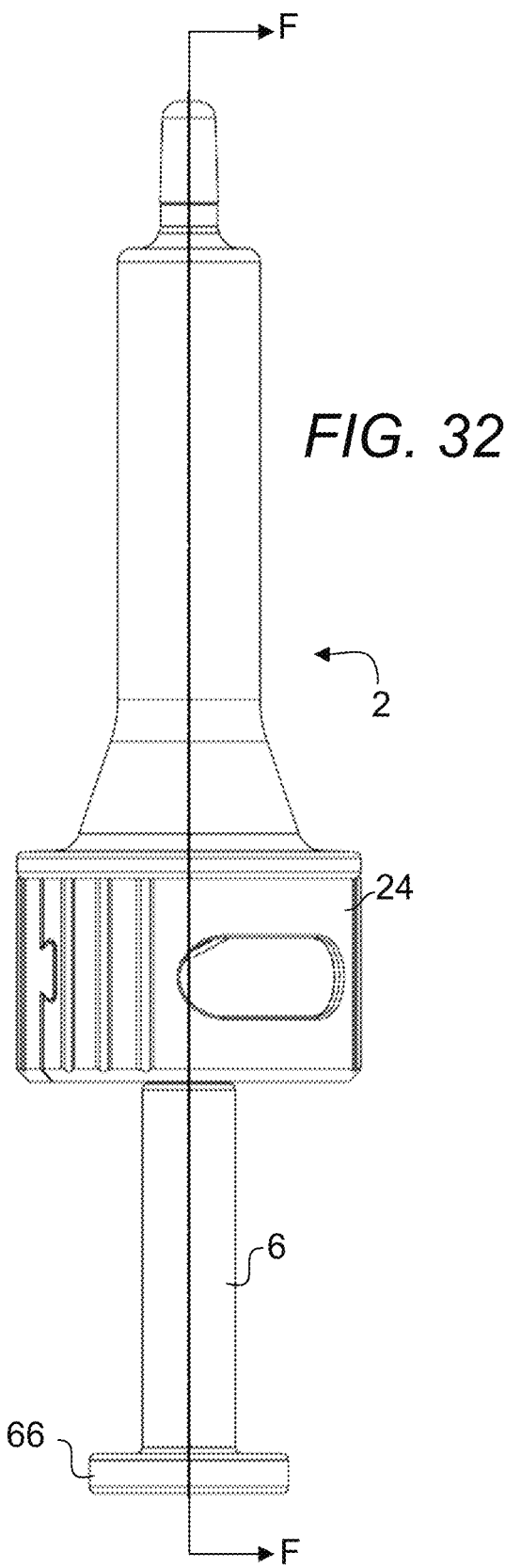
FIG. 32 is a longitudinal view of one embodiment according to a present syringe in a pre-administration condition.
Figure 33:
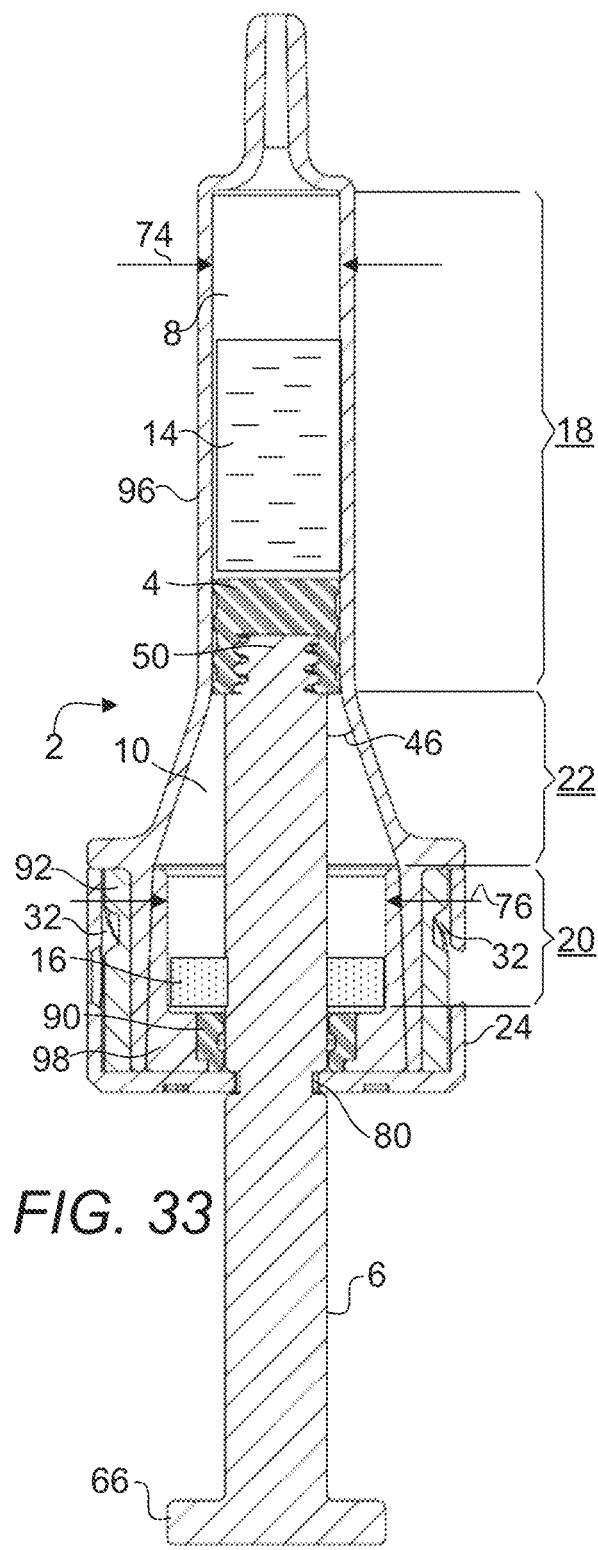
FIG. 33 is a longitudinal cross-sectional view of the embodiment of a present syringe of FIG. 32 as taken along line F-F of FIG. 32.

FIG. 32 is a longitudinal view of one embodiment according to a present syringe 2 in a pre-administration condition. FIG. 33 is a longitudinal cross-sectional view of the embodiment of a present syringe of FIG. 32 as taken along line F-F of FIG. 32. Here, a first part encompasses the first hollow cylinder 18, second hollow cylinder 20 and tube 22. A second part 98, formed in the shape of a cup, is configured to be coupled to the first part 96, e.g., with an adhesive. The screw thread grooves 32 are disposed on a sleeve 92 attached, e.g., with an adhesive, to a bottom portion of the first part 96. In one example, the first and second parts 96, 98 are both made from glass.

The detailed description refers to the accompanying drawings that show, by way of illustration, specific aspects and embodiments in which the present disclosed embodiments may be practiced. These embodiments are described in sufficient detail to enable those skilled in the art to practice aspects of the present invention. Other embodiments may be utilized, and changes may be made without departing from the scope of the disclosed embodiments. The various embodiments can be combined with one or more other embodiments to form new embodiments. The detailed description is, therefore, not to be taken in a limiting sense, and the scope of the present invention is defined only by the appended claims, with the full scope of equivalents to which they may be entitled. It will be appreciated by those of ordinary skill in the art that any arrangement that is calculated to achieve the same purpose may be substituted for the specific embodiments shown. This application is intended to cover any adaptations or variations of embodiments of the present invention. It is to be understood that the above description is intended to be illustrative, and not restrictive, and that the phraseology or terminology employed herein is for the purpose of description and not of limitation. Combinations of the above embodiments and other embodiments will be apparent to those of skill in the art upon studying the above description. The scope of the present disclosed embodiments includes any other applications in which embodiments of the above structures and fabrication methods are used. The scope of the embodiments should be determined with reference to the appended claims, along with the full scope of equivalents to which such claims are entitled.

What is claimed herein is:

1. A syringe comprising:
   (a) a first hollow cylinder comprising a first end, a second end and a first inner diameter;
   (b) a second hollow cylinder comprising a first end, a second end and a second inner diameter, wherein said second end of said second hollow cylinder is fixed with respect to said first end of said second hollow cylinder;
   (c) a tube comprising a first end having said first inner diameter and a second end having said second inner diameter, wherein said tube is configured to connect said first hollow cylinder at said second end of said first hollow cylinder and said second hollow cylinder at said first end of said second hollow cylinder; and
   (d) a piston configured to slide within said first hollow cylinder, said tube and said second hollow cylinder, a first position of said piston within said first hollow cylinder defining a first space between said piston and said first end of said first hollow cylinder and a second space between said piston and said second end of said second hollow cylinder, wherein said first space is isolated from said second space;
   (e) a cup configured for holding a second substance prior to being fixedly coupled to said second end of said second hollow cylinder such that said second end of said second hollow cylinder is fixed with respect to said first end of said second hollow cylinder, wherein a communication of a first substance within said first space and said second substance within said second space is enabled through said tube by withdrawing said piston from said first space and said syringe further comprises a rod attached to said piston and a stopper removably attached to said rod and said second hollow cylinder to allow a first action to remove said stopper to cause a concurrent second action that enables said communication.

2. The syringe of claim 1, further comprising a needle disposed on said first end of said first hollow cylinder for delivering at least one of the first substance and a mixture of the first substance and the second substance.

3. The syringe of claim 1, wherein said first hollow cylinder further comprises a central axis, said second hollow cylinder further comprises a central axis, said tube further comprises a central axis and said piston further comprises a central axis, wherein said central axis of said first hollow cylinder is coaxially disposed with said central axis of said second hollow cylinder, said central axis of said tube and said piston.

4. The syringe of claim 1, wherein said second diameter is greater than said first diameter.

5. The syringe of claim 1, wherein said first hollow cylinder further comprises a central axis, said syringe further comprises a safety shield configured to be slidable along a path parallel to said central axis of said first hollow cylinder from a first unlocked position to a second locked position disposed in a manner to shield a needle disposed on said first end of said first hollow cylinder from contact with a user.

6. A syringe comprising:
   (a) a first hollow cylinder comprising a first end, a second end and a first inner diameter;
   (b) a second hollow cylinder comprising a first end, a second end, a second inner diameter and a central axis;
   (c) a tube comprising a first end having said first inner diameter and a second end having said second inner diameter, wherein said tube is configured to connect said first hollow cylinder at said second end of said first hollow cylinder and said second hollow cylinder at said first end of said second hollow cylinder and said second inner diameter is greater than said first inner diameter; and
   (d) a piston configured to slide within said first hollow cylinder, said tube and said second hollow cylinder, a first position of said piston within said first hollow cylinder defining a first space between said piston and said first end of said first hollow cylinder and a second space between said piston and said second end of said second hollow cylinder, wherein said first space is isolated from said second space, wherein a communication of a first substance within said first space and a second substance within said second space is enabled through said tube by withdrawing said piston from said first space and said syringe further comprises a rod attached to said piston and a stopper removably attached to said rod and said second hollow cylinder to allow a first action to remove said stopper to cause a second concurrent action that enables said communication.

\* \* \* \* \*